(12) United States Patent
Day et al.

(10) Patent No.: US 10,058,532 B2
(45) Date of Patent: *Aug. 28, 2018

(54) METHODS OF PREVENTING PROGRESSION TO TYPE 2 DIABETES MELLITUS

(71) Applicant: Vivus, Inc., Campbell, CA (US)

(72) Inventors: Wesley Day, Cupertino, CA (US); Barbara Troupin, Redwood, CA (US)

(73) Assignee: Vivus, Inc., Campbell, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/639,972

(22) Filed: Jun. 30, 2017

(65) Prior Publication Data
US 2018/0055818 A1    Mar. 1, 2018

Related U.S. Application Data

(63) Continuation of application No. 14/509,297, filed on Oct. 8, 2014, now Pat. No. 9,724,327.

(60) Provisional application No. 61/888,490, filed on Oct. 8, 2013.

(51) Int. Cl.
*A61K 31/357* (2006.01)
*A61K 31/137* (2006.01)

(52) U.S. Cl.
CPC .......... *A61K 31/357* (2013.01); *A61K 31/137* (2013.01)

(58) Field of Classification Search
CPC combination set(s) only.
See application file for complete search history.

(56) References Cited

U.S. PATENT DOCUMENTS

| | | | |
|---|---|---|---|
| 8,580,298 B2 | 11/2013 | Najarian et al. | |
| 8,580,299 B2 | 11/2013 | Najarian et al. | |
| 9,724,327 B2 * | 8/2017 | Day | A61K 31/357 |
| 2009/0304785 A1 | 12/2009 | Najarian et al. | |
| 2009/0304789 A1 | 12/2009 | Najarian et al. | |
| 2010/0215739 A1 | 8/2010 | Najarian et al. | |

FOREIGN PATENT DOCUMENTS

CN        102112126 A      6/2011

OTHER PUBLICATIONS

Alberti, K.G., et al., "Harmonizing the metabolic syndrome: a joint interim statement of the International Diabetes Federation Task Force on Epidemiology and Prevention National Heart, Lung, and Blood Institute; American Heart Association; World Heart Federation; International Atherosclerosis Society; and International Association for the Study of Obesity", *Circulation*, 120(16):1640-1645 (2009).
Allison, D.B., et al., "Controlled-Release Phentermine/Topiramate in Severely Obese Adults: A Randomized Controlled Trial (EQUIP)", *Obesity*, 20(2):330-342 (2012).
Bakris, G., et al., "Risk Factor Assessment for New Onset Diabetes: Literature Review", *Diabetes, Obesity and Metabolism*, 11(3):177-187 (2009).
Carlsson, L.M., et al., "Bariatric Surgery and Prevention of Type 2 Diabetes in Swedish Obese Subjects", *N. Eng. J. Med.*, 367(8):695-704 (2012).
Christophi, C.A, et al., "10-year follow-up of diabetes incidence and weight loss in the Diabetes Prevention Program Outcomes Study", *Lancet*, 374:1677-1686 (2009).
Colquitt, J.L., et al., "Surgery for obesity (Review)", *The Cochrane Collaboration, The Cochrane Library*, 15(2):CD003641 (2009).
Elobeid, M.A., et al., "Missing Data in Randomized Clinical Trials for Weight loss: Scope of the Problem, State of the Field, and Performance of Statistical Methods", *PLoS One*, 4(8)(e6624)1-11 (2009).
Gadde, K.M., et al., "Effects of low-dose, controlled-release, phentermine plus topiramate combination on weight and associated comorbidities in overweight and obese adults (CONQUER): a randomised, placebo-controlled, phase 3 trial", *Lancet*, 377:1341-1352 (2011).
Garvey et al., "Prevention of Type 2 Diabetes in Subjects With Prediabetes and Metabolic Syndrome Treated with Phentermine and Topiramate Extended Release", *Diabetes Care*, 37(4):912-921 (2014).
Garvey, W.T., et al., "Two-year sustained weight loss and metabolic benefits with controlled-release phentermine/topiramate in obese and overweight adults (SEQUEL): a randomized, placebo-controlled, phase 3 extension study", *Am J Clin Nutr.*, 95(2):297-308 (2012).
Grundy, S.M., et al., "Diagnosis and Management of the Metabolic Syndrome: An American Heart Association/National Heart, Lung, and Blood Institute Scientific Statement", *Circulation*, 112(17):2735-2752 (2005).
Hamman, R.F., et al., "Effect of Weight Loss with Lifestyle Intervention on Risk of Diabetes", *Diabetes Care*, 29(9):2102-2107 (2006).
Hussain, S.S. and Bloom, S.R., "The Pharmacological Treatment and Management of Obesity", *Postgrad Med.*, 123(1):34-44 (2011).
Kofman, M.D., et al., "Maladaptive Eating Patterns, Quality of Life, and Weight Outcomes Following Gastric Bypass: Results of an Internet Survey", *Obesity*, 18(10):1938-1943 (2010).
Laaksonen, D.E., et al., "Physical Activity in the Prevention of Type 2 Diabetes: The Finnish Diabetes Prevention Study", *Diabetes*, 54:158-165 (2005).
Li, G., et al., "The long-term effect of lifestyle interventions to prevent diabetes in the China Da Qing Diabetes Prevention Study: a 20-year follow-up study", *Lancet*, 371:1783-1789 (2008).
Lindström, J., et al., "Sustained reduction in the incidence of type 2 diabetes by lifestyle intervention: follow-up of the Finnish Diabetes Prevention Study", *Lancet*, 368:1673-1679 (2006).
Lorenzo, C., et al., "The Metabolic Syndrome as Predictor of Type 2 Diabetes: The San Antonio Heart Study", *Diabetes Care*, 26(11):3153-3159 (2003).

(Continued)

*Primary Examiner* — Rei Tsang Shiao
(74) *Attorney, Agent, or Firm* — Cooley LLP; Ivor R. Elrifi; Matthew Pavao

(57) ABSTRACT

The present invention provides compositions and methods for delaying or preventing progression to type 2 diabetes mellitus in individuals with prediabetes and metabolic syndrome.

16 Claims, 8 Drawing Sheets

(56) References Cited

OTHER PUBLICATIONS

Nathan, et al., "Impaired Fasting Glucose and Impaired Glucose Tolerance: Implications for Care", Diabetes Care, 30(3):753-759 (2007).
Norris, S.L. et al., "Long-term non-pharmacological weight loss interventions for adults with prediabetes (Review)", *The Cochrane Collaboration, The Cochrane Library*, 18(2):CD005270, 125 pages (2005).
Pan, X.R., et al., "Effects of Diet and Exercise in Preventing NIDDM in People with Impaired Glucose Tolerance: The Da Qing IGT and Diabetes Study", *Diabetes Care*, 20(4):537-544 (1997).
Pi-Sunyer et al., "The Medical Risks of Obesity", *Postgrad Med*, 121(6):21-33 (2009).
Sutherland, J.P., et al., "The Metabolic Syndrome and Inflammation", *Metabolic Syndrome and Related Disorders*, 2(2):82-104 (2004).
Wang, B. et al. "Prevalence of Metabolically Healthy Obese and Metabolically Obese but Normal Weight in Adults Worldwide: A Meta-Analysis", Horm Metab Res 47: 839-845 (2015).

\* cited by examiner

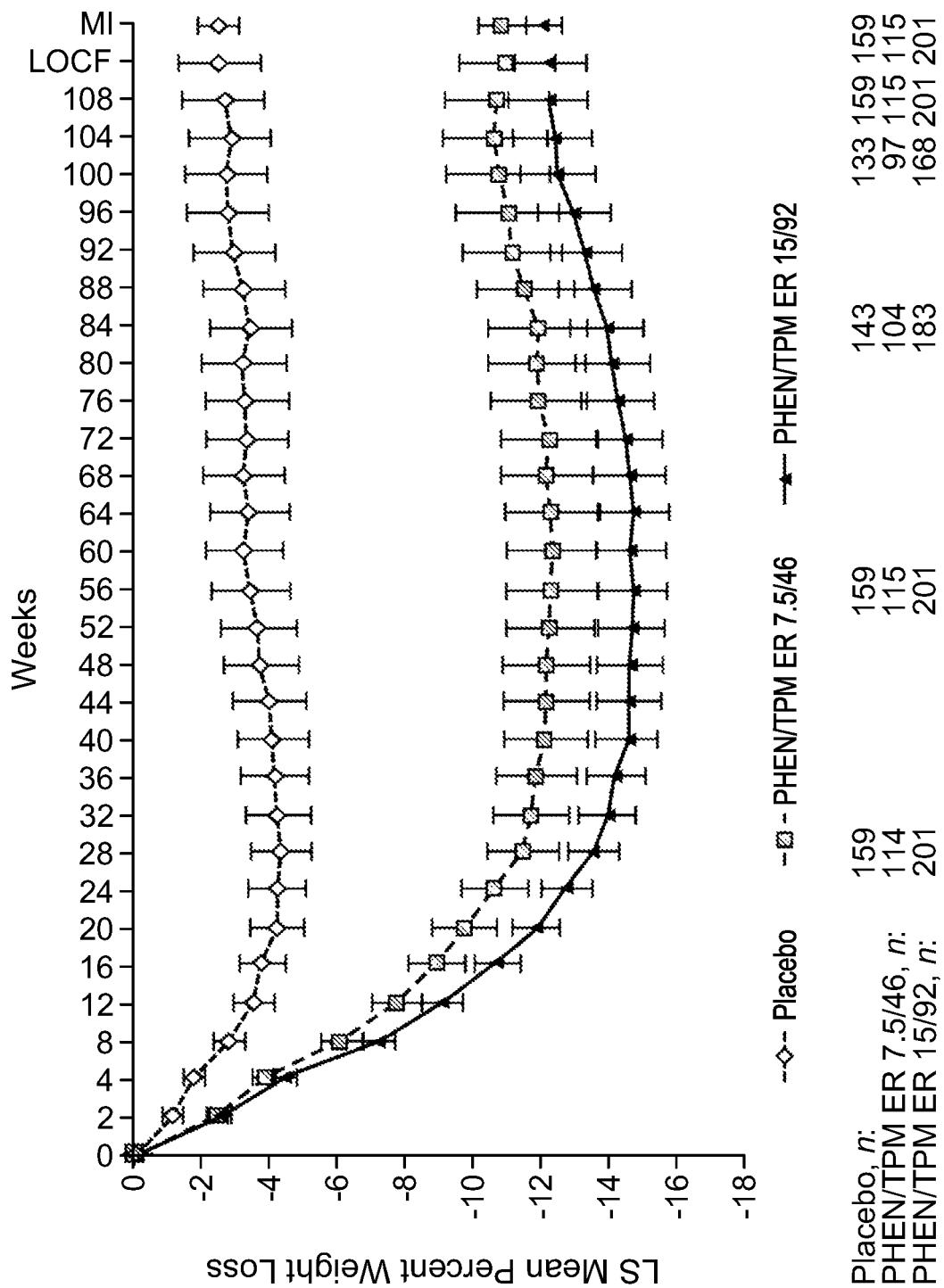

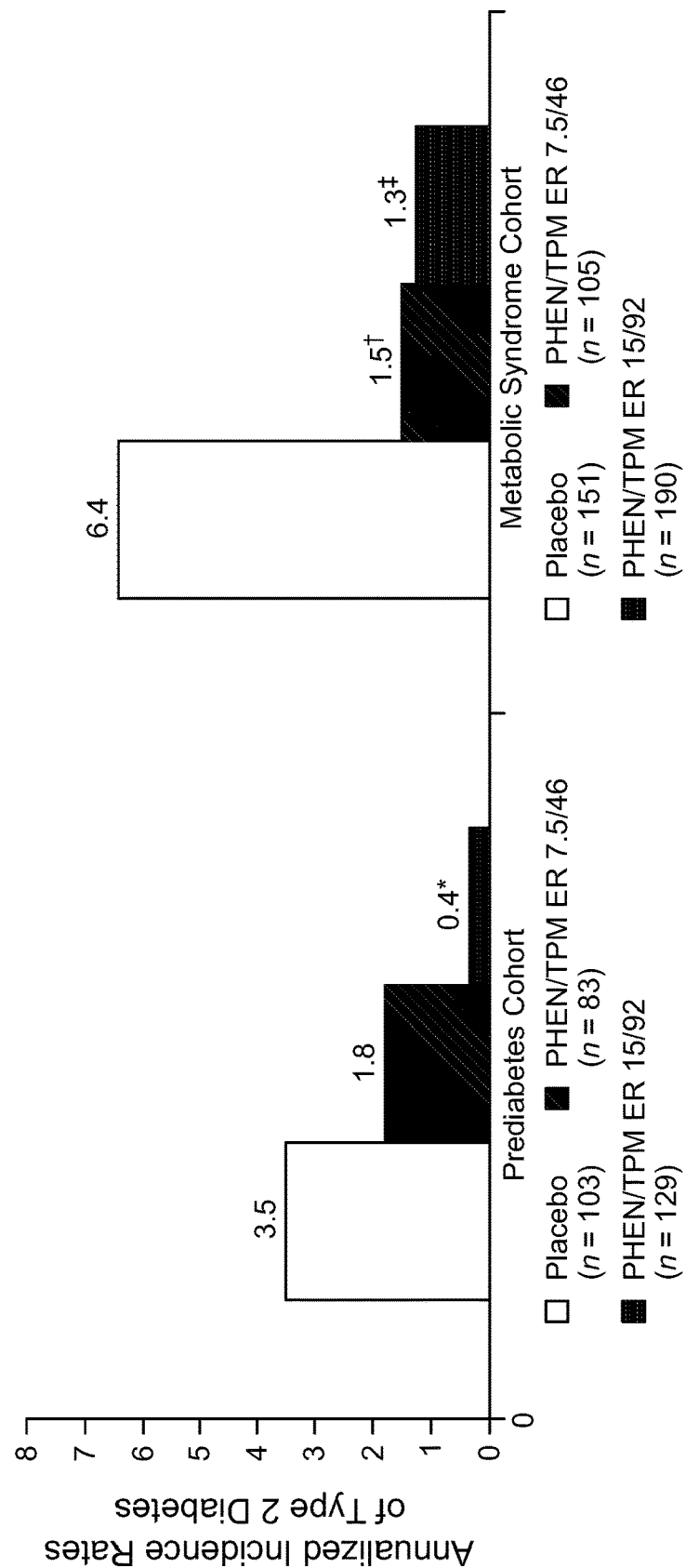

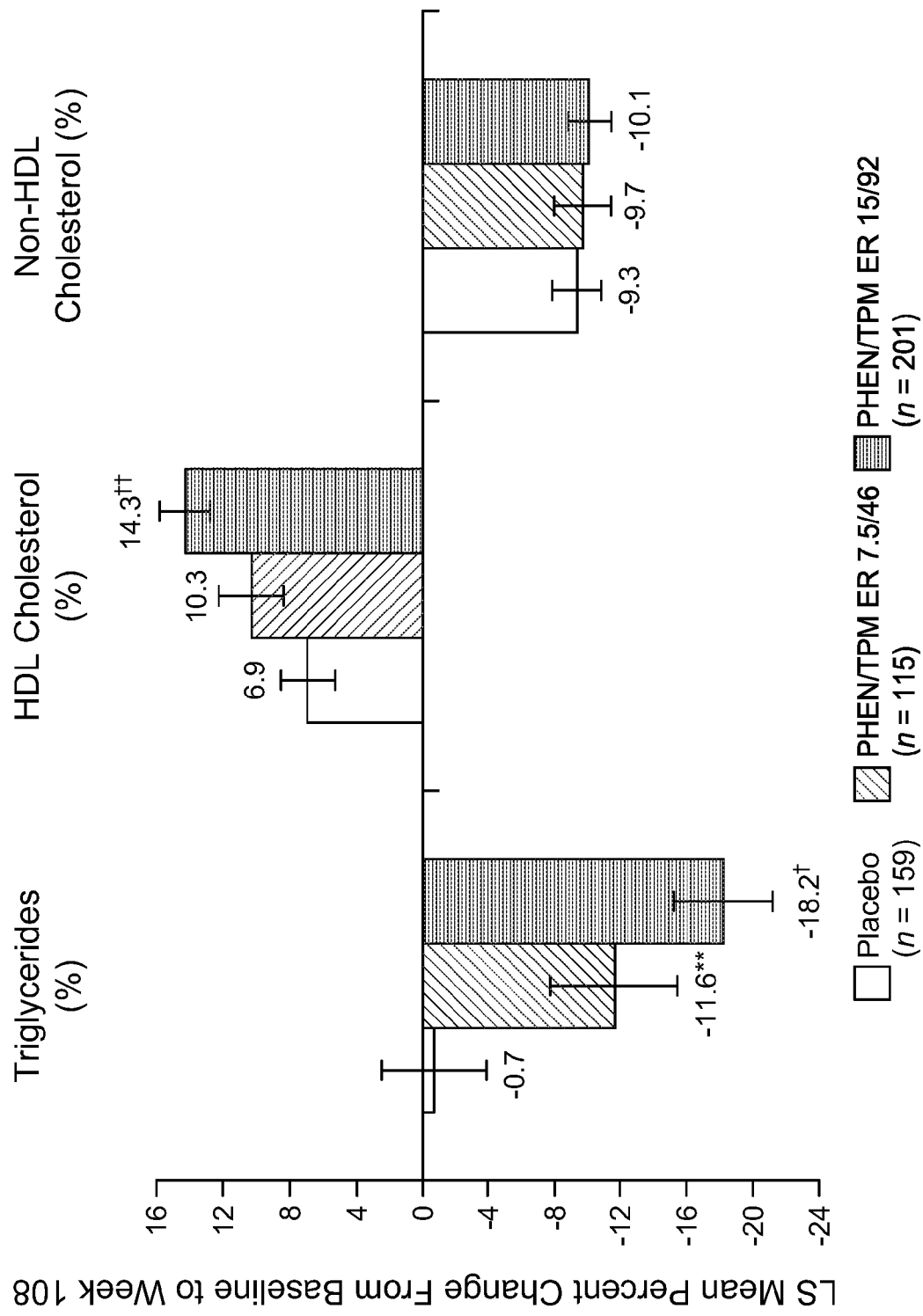

METHODS OF PREVENTING PROGRESSION TO TYPE 2 DIABETES MELLITUS

CROSS-REFERENCE TO RELATED APPLICATIONS

This application is a continuation of U.S. application Ser. No. 14/509,297, which was filed on Oct. 8, 2014, which claims priority to, and the benefit of, U.S. Provisional Patent Application Ser. No. 61/888,490, filed Oct. 8, 2013, the contents of each of which are herein incorporated by reference in their entirety.

FIELD OF THE INVENTION

The disclosure relates to, among other things, methods for preventing progression to type 2 diabetes mellitus in individuals with prediabetes and metabolic syndrome. Individuals are treated with a combination of phentermine and topiramate extended release (PHEN/TPM ER), which has been shown to induce weight loss and improve glycemia in overweight subjects and obese subjects with one or more weight related comorbidities. Treatment with PHEN/TPM ER results in markedly reduced progression to type 2 diabetes in overweight or obese patients with prediabetes and/or metabolic syndrome and results in improvements in multiple cardiometabolic disease risk factors.

BACKGROUND OF THE INVENTION

The increased prevalence of type 2 diabetes mellitus (also referred to herein as T2DM or type 2 diabetes), together with its burden of patient suffering and societal costs, underscores the importance of finding effective strategies for both treatment and prevention. T2DM is characterized by high blood glucose levels caused by a lack of insulin or the body's inability to efficiently use insulin. Two clinical constructs for identifying individuals at high risk of future T2DM are prediabetes and metabolic syndrome (MetS). Prediabetes is a state of dysglycemia characterized by impaired fasting glucose (IFG) and/or impaired glucose tolerance (IGT). A diagnosis of prediabetes may be made if an individual's glucose is higher than normal but not high enough to be diagnosed as diabetes. It is estimated that 79 million Americans aged 20 years or older have prediabetes, with 25% progressing to T2DM within 3-5 years (Nathan, et al. *Diabetes Care.* 2007; 30(3):753-759). ENREF4 T2DM is associated with abdominal obesity and insulin resistance (diagnostic criteria were established by the Advanced Treatment Panel III of the National Cholesterol Education Program). There are a number of risk factors that increase an individual's risk for T2DM including, for example, being over age 45, being overweight or obese, having a parent, brother or sister with diabetes, a family background that is African American, Alaska Native, American Indian, Asian American, Hispanic/Latino, or Pacific Islander, having a history of gestational diabetes, giving birth to a baby weighing more than 9 pounds, blood pressure of 130/85 or 140/90 or higher, HDL lower than 35 or lower than 40 (for males) or lower than 50 for females or triglyceride level above 150 or above 250, inactive lifestyle, polycystic ovary syndrome, a previous diagnosis of prediabetes, for example HbA1c level of 5.7 to 6.4%, impaired fasting glucose (IFG) or impaired glucose tolerance (IGT), another clinical conditions associated with insulin resistance, such as a condition called acanthosis nigricans, characterized by a dark, velvety rash around my neck or armpits, or a history of cardiovascular disease. The more of these risk factors present in a patient the higher the patient's risk of developing T2DM. HbA1c refers to glycated haemoglobin (A1c), which identifies average plasma glucose concentration and can be used to get an overall picture of what an individual's average blood sugar levels have been over a period of time.

MetS is a cluster of risk factors for cardiovascular disease including the following risk factors (1) a large waistline (at least 102 cm or 40 inches for males and at least 88 cm or 35 inches for females), also referred to as abdominal obesity, (2) high triglyceride levels (greater than 150 or 250) or using medicine to treat high triglycerides, (3) low HDL cholesterol levels (lower than 35 or lower than 40 (for males) or lower than 50 for females) or using medicine to treat low HDL cholesterol, (4) high blood pressure (above 130/85 or above 140/90) or using medicine to treat high blood pressure, and (5) high fasting blood sugar (also referred to as impaired fasting glucose (IFG)) or using medicine to treat high blood sugar ((See Alberti K G, et al., *Circulation* 2009; 120(16): 1640-1645; Bakris G, et al., *Diabetes Obes Metab.* 2009; 11(3):177-187; Expert Panel on Detection, Evaluation, and Treatment of High Blood Cholesterol in Adults, *JAMA* 2001; 285(19):2486-2497; and Grundy S M, et al. *Circulation* 2005; 112(17):2735-2752). A diagnosis of MetS generally required a diagnosis of at least three of the five metabolic risk factors listed above. Individuals with MetS are at a 5-fold increased risk of developing T2DM (Alberti K G, et al. 2009). Because IFG is one of the traits used to identify MetS, overlap with criteria for prediabetes exists, and the risk of progression to T2DM is further increased in individuals who satisfy the criteria for both MetS and prediabetes. Lorenzo C, et al., *Diabetes Care.* 2003; 26(11):3153-3159. Thus, effective treatment of these at-risk individuals is important for the prevention of T2DM.

Sustained loss of 5% to 10% of body weight in obese and overweight patients has proven to be effective in preventing progression from prediabetes and MetS to T2DM and also ameliorates the cardiometabolic disease process, as shown by an increase in insulin sensitivity and a reduction in cardiovascular disease risk factors. However, achieving sustained weight loss at a clinically meaningful level sufficient to reduce risk remains a challenge for many patients. The primary approach to treating obesity and its related complications involves lifestyle modifications, including reductions in caloric intake (by 500-4000 calories/day) combined with increases in physical activity. Bariatric surgery can also be an effective weight-loss option for patients meeting specific criteria and may reduce the incidence of T2DM, Colquitt J L, et al., *Cochrane Database Syst Rev.* 2009; 15(2):CD003641, Hussain S S, Bloom S R, *Postgrad Med.* 2011; 123(1):34-44 and Carlsson L M, et al., *N Engl J Med.* 2012; 367(8):695-704 but the approach entails risks associated with surgery, nutritional deficiencies, and weight regain in some patients. Kofman M D, et al., *Obesity (Silver Spring).* 2010; 18(10):1938-1943.

In patients for whom lifestyle changes alone are insufficient and bariatric surgery is not an option, pharmacotherapies may be considered. Phentermine and topiramate extended-release (PHEN/TPM ER; QSYMIA®; VIVUS, Inc., Mountain View, Calif.) has been shown to induce significant weight loss when combined with lifestyle modification in overweight/obese adults. See, for example, Allison D B, et al., *Obesity (Silver Spring),* 2012; 20(2):330-342. The CONQUER study assessed effectiveness of PHEN/TPM ER for weight loss in overweight/obese adults with two or more weight-related comorbidities over 56 weeks (ClinicalTrials.gov, NCT00553787)(Gadde K M, et al., *Lancet.* 2011; 377(9774):1341-1352) and was followed by SEQUEL, a 52-week blinded extension study (ClinicalTrials.gov, NCT00796367)(Garvey W T, et al., *Am J Clin Nutr.* 2012; 95(2):297-308). In order to assess the ability of PHEN/TPM ER to reduce progression to T2DM and improve manifestations of cardiometabolic disease in patients at high risk of developing T2DM, a subpopulation of patients meeting the criteria at baseline for prediabetes and/or MetS who elected to enroll in SEQUEL was analyzed.

In addition to being related to incidence of various diseases, obesity can increase the risk of death from hypertension, dyslipidemia, diabetes, such as type II diabetes mellitus, coronary artery disease, heart disease, stroke, gallbladder disease, osteoarthritis, liver disease, and cancers, such as endometrial, breast, prostate, and colon cancers (see, for example, Pi-Sunyer et al. *Postgrad Med* 2009:121:21-33).

Topiramate, a sulfamate-substituted monosaccharide with the chemical name 2,3,4,5-bis-O-(1methyletylidene)-β-D-fructopyranose sulfamate, has been reported for use in treating obesity and promoting weight loss, for example, in U.S. Pat. Pub. 2009/0304785, and is also marketed for treating migraine headaches and seizure related disorders. A variety of dosages of topiramate can be used for these purposes, depending on the weight, age, gender, and other characteristics of the subject. Although efficacious for these purposes, topiramate is known to have harmful side effects in some subjects. Furthermore, some subjects do not respond to topiramate treatment for obesity. Thus, there is a need for a dosing regimen for topiramate that minimizes subjects' exposure to topiramate while providing one or more indications of whether a particular subject is likely to experience harmful side effects and/or respond to topiramate treatment. The embodiments described herein can meet these and other needs.

SUMMARY OF THE INVENTION

Methods for delaying the progression of patients at risk for developing type 2 diabetes mellitus are disclosed. The methods comprise administering to a patient that has been diagnosed with prediabetes or MetS, or are otherwise identified as being at high risk to develop T2DM, an oral dosage form of immediate release phentermine and controlled release topiramate.

Preferred daily doses include 3.75 mg immediate release phentermine in combination with 23 mg controlled release topiramate (3.75/23), 7.5 mg immediate release phentermine in combination with 46 mg controlled release topiramate (7.5/46), 11.25 mg immediate release phentermine in combination with 69 mg controlled release topiramate (11.25/69), and 15 mg immediate release phentermine in combination with 92 mg controlled release topiramate (15/92).

The combination of phentermine and topiramate may be administered to the patient for a period of weeks, months or years and patients may increase doses over time. In one aspect the patient starts with a daily dose of 3.75/23 for 1 to 2 weeks then increases the dose to 7.5/46. The patient may maintain that dose for 1 to 3 months and then either stay on the 7.5/46 dose for up to 2 years or longer or increase to the 15/92 dose. Some patients, rather than increasing directly to the 15/92 dose from the 7.5/46 dose will take the 11.25/69 dose for a period of 1 to 2 weeks before moving to the 15/92 dose.

In a preferred aspect the patient has been identified as being at high risk of developing type 2 diabetes and the treatment prevents or delays the onset of type 2 diabetes. For those patients that then experience an onset of type 2 diabetes, the method of treatment prior to the onset reduces the severity of the symptoms experienced by the patient following the onset of type 2 diabetes. Although in many cases the at risk patient will be overweight (BMI greater than 25) or obese (BMI of 30 or higher), patients having normal weight (BMI 25 or less) that are at risk for diabetes may also benefit from the disclosed method of treatment.

Individuals may be diagnosed with prediabetes if they have one of the following: (i) HbA1c levels that are at least 5.7% but not greater than 6.4%; (ii) plasma glucose levels of not more than 11 mmol/L (200 mg/dl) but at least 7.8 mmol/L (140 mg/dl) as measured in an OGTT screening test (impaired glucose tolerance); or (iii) blood glucose levels less than or equal to 7.0 mmol/L (126 mg/dl) but higher than 6.1 mmol/L (110 mg/dl) (impaired fasting glucose).

Individual may be diagnosed with MetS if they have at least 3 of the following: (i) waist circumference of at least 102 cm if the patient is male or at least 88 cm if the patient is female; (ii) triglyceride level of 150 mg/dL or higher; (iii) HDL cholesterol levels below 40 mg/dL if the patient is a male or below 50 mg/dL if the patient is a female or taking lipid lowering medication; (iv) systolic blood pressure of 130 mm Hg or greater, or diastolic blood pressure of 85 mm Hg or greater or taking antihypertensive medication; and (v) fasting blood glucose levels of 100 mg/dL or greater or taking medication for elevated glucose. Patients that have been diagnosed with MetS may achieve remission of MetS if they no longer meet at least 3 of the identified criteria.

In some aspects the method may be used to lower hs-CRP values (high-sensitivity C-Reactive Protein) to 3.0 mg/L or less (higher levels are indicative of high risk for cardiovascular disease), lower fibrinogen levels to 400 mg/dL or less, and increase adiponectin concentrations from the starting levels for the patient prior to treatment, for example to greater than 20 mcg/mL for males and greater than 22 mcg/mL for females, in patients at risk for developing T2DM. The method of treatment may further achieve in patients diagnosed with prediabetes or MetS an improvement in at least one of the following: fasting glucose levels, fasting insulin levels, 2-hour post-oral glucose tolerance test (OGTT) glucose levels, fasting triglycerides levels and HDL-C levels.

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In the case of conflict, the present specification, including definitions, will control. In addition, the materials, methods, and examples are illustrative only and are not intended to be limiting. Other features and advantages of the invention will be apparent from the following detailed description and claims.

BRIEF DESCRIPTION OF THE DRAWINGS

FIG. 1 shows percent weight loss from baseline to week 108 in the cohort with prediabetes and/or metabolic syndrome at baseline assessed using least-squares mean percent weight loss in the intent-to-treat (ITT) population of subjects with prediabetes and/or metabolic syndrome.

FIG. 2B shows annualized incidence rates of type 2 diabetes at study end in the prediabetes cohort and the Metabolic Syndrome cohort for the SEQUEL study (ITT).

FIG. 3C shows least-squares mean percent change from baseline in lipid parameters in the prediabetes and/or Metabolic Syndrome cohort.

DETAILED DESCRIPTION

Figure 2A:
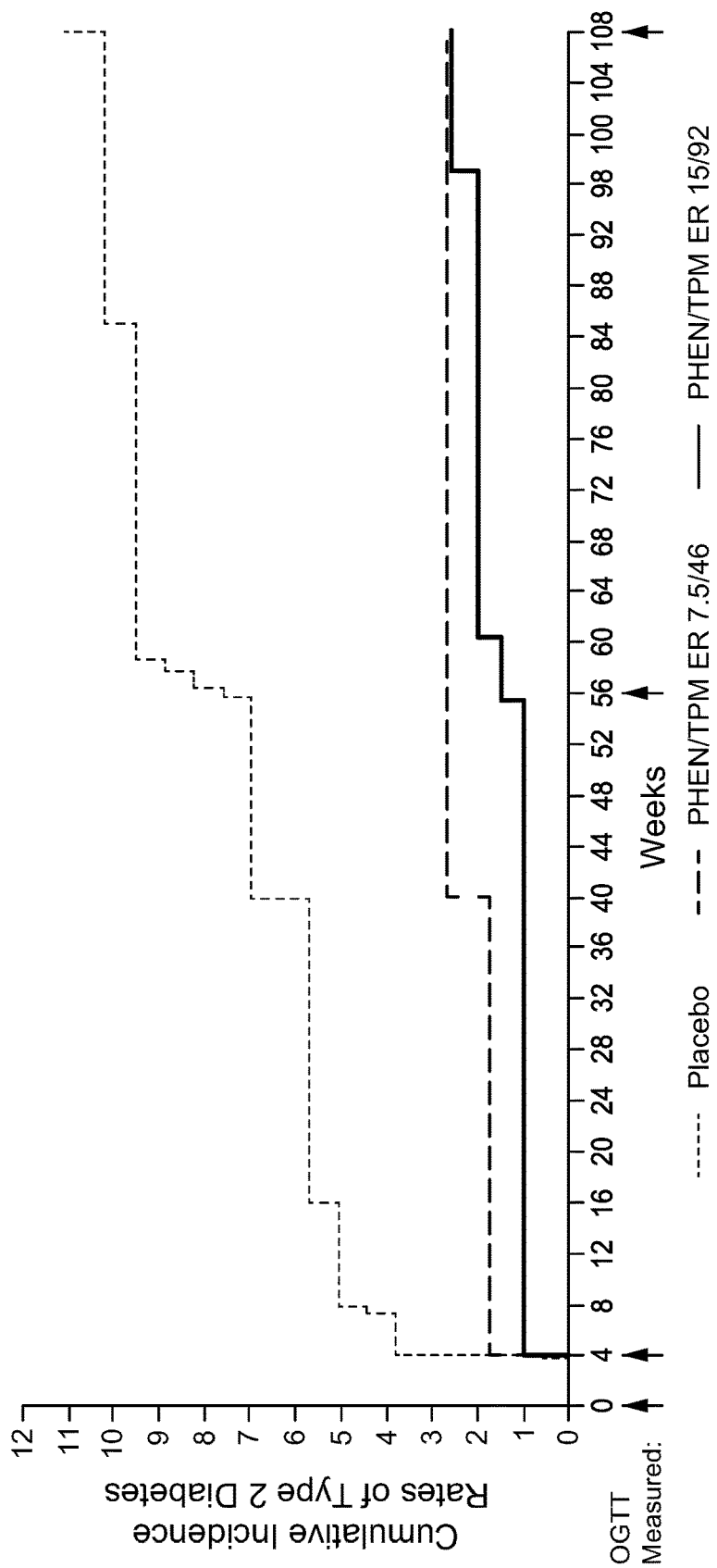
FIG. 2A shows cumulative incidence rates of type 2 diabetes at study end (Kaplan-Meier) in the prediabetes and/or Metabolic Syndrome cohort of the SEQUEL study from baseline to week 108 (ITT).

In this application, including the appended claims, the singular forms "a," "an," and "the" are often used for convenience. However, it should be understood that these singular forms include the plural unless otherwise specified. It should also be understood that all patents, publications, journal articles, technical documents, and the like, referred to in this application, are hereby incorporated by reference in their entirety and for all purposes.

Unless otherwise defined, all terms used in this application should be given their standard and typical meanings in the art, and are used as those terms would be used by a person of ordinary skill in the art at the time of the invention.

"Active agent" as used herein encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds as will be discussed infra. Therefore, reference to "phentermine," for example, encompasses not only phentermine per se but also salts and other derivatives of phentermine, e.g., phentermine hydrochloride. It is to be understood that when amounts or doses are specified, that those amounts or doses refer to the amount or dose of active agent per se and not to a salt or the like. For example, when it is indicated that a dose or amount of phentermine is 7.5 mg, that would correspond to 9.84 phentermine hydrochloride and not 7.5 phentermine hydrochloride.

"Administering" as used herein includes to any route of administration, for example, oral, parenteral, intramuscular, transdermal, intravenous, inter-arterial, nasal, vaginal, sublingual, subungal, etc. Administering can also include prescribing a drug to be delivered to a subject, for example, according to a particular dosing regimen, or filling a prescription for a drug that was prescribed to be delivered to a subject, for example, according to a particular dosing regimen.

"Body Mass Index" or "BMI" as used herein is an index of weight-for-height that is commonly used to classify overweight and obesity in adults. BMI may be calculated by multiplying an individual's weight, in kilograms, by height, in meters. Currently the CDC and WHO define obesity as having a BMI of 30 or higher. A BMI between 25 and 29.9 is considered overweight. A BMI over 40 is sometimes characterized as morbidly obese. Individuals having a BMI between 30 and 35 may also be referred to as moderately obese, from 35 to 40 severely obese and over 40 very severely obese.

A "daily dose" of a particular material refers the amount of the material administered in a day. A daily dose can be administered as a single dose or as multiple doses. When a daily dose is administered as multiple doses, the daily dose is the sum of the amount of material administered in all of the multiple doses that are administered over the course of one day. For example, a daily dose of 12 mg can be administered in a single 12 mg dose once per day, in 6 mg doses administered twice per day, in 4 mg doses administered three times per day, in 2 mg doses administered six times per day, etc. The multiple doses can be the same or different doses of the material, unless otherwise specified. When a daily dose is administered as multiple doses, the multiple doses can be administered by the same or different route of administration, unless otherwise specified. Thus, a daily dose of 12 mg can include, for example, a 10 mg intramuscular dose and a 2 mg oral dose administered over the course of one day.

The term "dosage form" denotes any form of a pharmaceutical composition that contains an amount of active agent sufficient to achieve a therapeutic effect with a single administration. When the formulation is a tablet or capsule, the dosage form is usually one such tablet or capsule, although this is not required unless otherwise specified. The frequency of administration that will provide the most effective results in an efficient manner without overdosing will vary with the characteristics of the particular active agent, including both its pharmacological characteristics and its physical characteristics, such as hydrophilicity.

The term "controlled release" refers to a drug-containing formulation or fraction thereof in which release of the drug is not immediate, i.e., with a "controlled release" formulation, administration does not result in immediate release of the drug into an absorption pool. The term is used interchangeably with "nonimmediate release" as defined in Remington: The Science and Practice of Pharmacy, Nineteenth Ed. (Easton, Pa.: Mack Publishing Company, 1995). In general, the term "controlled release" as used herein includes sustained release, modified release and delayed release formulations.

The term "sustained release" (synonymous with "extended release") is used in its conventional sense to refer to a drug formulation that provides for gradual release of a drug over an extended period of time, and that preferably, although not necessarily, results in substantially constant blood levels of a drug over an extended time period. The term "delayed release" is also used in its conventional sense, to refer to a drug formulation which, following administration to a patient provides a measurable time delay before drug is released from the formulation into the patient's body.

Administration of one compound "with" a second compound, as used herein, includes but is not limited to cases where the two compounds are administered simultaneously or substantially simultaneously. For example, administration of a first compound with a second compound can include administering the first compound in the morning and administering the second compound in the evening, as well as administering the first and second compounds in the same dosage form or in two different dosage forms that at the same or nearly the same time.

"Topiramate" as used herein includes not only the chemical compound 2,3:4,5-di-O-isopropylidene-β-D-fructopyranose sulfamate, but also all stereoisomers, such as enantiomers and diasteriomers, thereof, as well as salts, mixed salts, polymorphs, solvates, including mixed hydrates and mixed solvates, of one or more stereoisomers or mixtures of stereoisomers. The molecular formula is $C_{12}H_{21}NO_8S$ and its molecular weight is 339.4. Topiramate is a white to off-white crystalline powder with a bitter taste. It is freely soluble in methanol and acetone, sparingly soluble in pH 9 to pH 12 aqueous solutions and slightly soluble in pH 1 to pH 8 aqueous solutions.

"Phentermine" as used herein includes not only the chemical compound 2-methyl-1-phenylpropan-2-amine, but also all stereoisomers, such as enantiomers and diasteriomers, thereof, as well as salts, mixed salts, polymorphs, solvates, including mixed hydrates and mixed solvates, of one or more stereoisomers or mixtures of stereoisomers. The chemical name of phentermine hydrochloride is α,α-dimethylphenethylamine hydrochloride. The molecular formula is $C_{10}H_{15}N \cdot HCl$ and its molecular weight is 185.7 (hydrochloride salt) or 149.2 (free base). A dosage of 3.75 mg phentermine is preferably in the form of 4.92 mg phentermine hydrochloride and similarly a dosage of 7.5 mg phentermine is preferably in the form of 9.84 mg phentermine hydrochloride, a dosage of 11.25 mg phentermine is preferably in the form of 14.76 mg phentermine hydrochloride and a dosage of 15 mg phentermine is preferably in the form of 19.68 mg phentermine hydrochloride.

A "subject" or multiple "subjects" can be members of any species, typically human. The subjects of all experiments and studies discussed herein were human except when otherwise indicated.

The term "sustained release" (synonymous with "extended release") is used in its conventional sense to refer to a drug formulation that provides for gradual release of a drug over an extended period of time, and that preferably, although not necessarily, results in substantially constant blood levels of a drug over an extended time period. The term "delayed release" is also used in its conventional sense, to refer to a drug formulation which, following administration to a patient provides a measurable time delay before drug is released from the formulation into the patient's body.

The term "unit dosage forms" as used herein refers to physically discrete units suited as unitary dosages for the individuals to be treated. That is, the compositions are formulated into discrete dosage units each containing a predetermined, "unit dosage" quantity of an active agent calculated to produce the desired therapeutic effect in association with the required pharmaceutical carrier. The specifications of unit dosage forms of the invention are dependent on the unique characteristics of the active agent to be delivered. Dosages can further be determined by reference to the usual dose and manner of administration of the ingredients. It should be noted that, in some cases, two or more individual dosage units in combination provide a therapeutically effective amount of the active agent, e.g., two tablets or capsules taken together may provide a therapeutically effective dosage of topiramate, such that the unit dosage in each tablet or capsule is approximately 50% of the therapeutically effective amount.

A suitable daily dose of topiramate extended-release is in the range of 10 mg to 150 mg. For example, 10 mg, 20 mg, 30 mg, 60 mg, 90 mg, 120 mg, 150 mg, or the like is administered to a patient as a daily dosage. In another example, 23 mg, 46 mg, 69 mg and 92 mg or the like is administered to a patient as a daily dosage. In certain embodiments, the daily dosage of topiramate extended release is in the range of 10 mg to 100 mg. Each of the aforementioned "daily dosages" is generally although not necessarily administered as a single daily dose.

A suitable daily dose of phentermine is in the range of 3 mg to 30 mg. For example, 3 mg, 5 mg, 8 mg, 10 mg, 12 mg, 15 mg, 20 mg, 25 mg, 30 mg, or the like is administered to a patient as a daily dosage. In another example, 3.75 mg, 7.5 mg, 11.25 mg and 15 mg or the like is administered to a patient as a daily dosage. Each of the aforementioned "daily dosages" is generally although not necessarily administered as a single daily dose.

Daily doses of PHEN/TPM ER that available include 3.75 mg phentermine with 23 mg topiramate extended-release, 7.5 mg phentermine with 46 mg topiramate extended-release, 11.25 mg phentermine with 69 mg topiramate extended-release, and 15 mg phentermine with 92 mg topiramate extended-release.

The patient may receive a specific dosage of PHEN/TPM ER over a period of weeks, months, or years, e.g., 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years and the like. In some embodiments the patient starts at one dose for a period of time and then increases doses after a period.

In one embodiment, a daily dose of phentermine can be administered with one or more of daily dose of about 23 mg topiramate, the daily dose of about 46 mg topiramate, the daily dose of about 69 mg topiramate, and the daily dose of about 92 mg topiramate. In another embodiment, a daily dose of about 3.75 mg of phentermine can be administered with the daily dose of about 23 mg of topiramate. In yet another embodiment, a daily dose of about 7.5 mg of phentermine can be administered with the daily dose of about 46 mg of topiramate. In still another embodiment, a daily dose of about 11.25 mg phentermine can be administered with the daily dose of about 69 mg of topiramate. In a further embodiment, a daily dose of about 15 mg of phentermine can be administered with the daily dose of about 92 mg of topiramate.

In a particular embodiment, phentermine can be administered in an immediate release form. In a specific embodiment, the topiramate can be administered in a controlled release form. In other embodiments, the controlled release form is a polymer coated bead. In an additional embodiment, phentermine can be administered in an immediate release form and the topiramate can be administered in a controlled release form. In some embodiments, the phentermine and the topiramate are administered in a single unit dosage form having a controlled release topiramate portion and an immediate release phentermine portion.

Treatment with PHEN/TPM ER may be used as a method for slowing progression, delaying onset of, or treating a metabolic disorder; improving glycemic control and/or for reducing fasting plasma glucose, postprandial plasma glucose, and/or glycosylated hemoglobin HbA1c; preventing, slowing, delaying, or reversing progression from impaired glucose tolerance, insulin resistance, and/or metabolic syndrome to type 2 diabetes mellitus; preventing, slowing progression, delaying, or treating complications of diabetes mellitus; preventing or treating the degeneration of pancreatic beta cells and/or for improving and/or restoring the functionality of pancreatic beta cells and/or restoring the functionality of pancreatic insulin secretion; or for maintaining and/or improving the insulin sensitivity and/or for treating or preventing hyperinsulinemia and/or insulin resistance, by administering to a patient a combination of phentermine and topiramate.

High-risk overweight or obese patients with prediabetes and/or metabolic syndrome who were taking PHEN/TPM ER over a two year period experienced reductions of up to 78.7% in the annualized incidence rate of type 2 diabetes, in addition to losing weight. The American Association of Clinical Endocrinologists recognizes obesity and prediabetes as significant risk factors for progression to diabetes and associated complications.

These data demonstrate that treatment with PHEN/TPM ER is highly effective in preventing progression to diabetes in an at-risk population, and underscores the observation that 10% weight loss achieves beneficial effects on metabolism and risk factors in patients with prediabetes and metabolic syndrome.

Treatment with PHEN/TPM ER may also reduce the severity of symptoms in patients that do progress to diabetes despite treatment PHEN/TPM ER prior to onset of diabetes. Symptoms of diabetes that may be reduced by PHEN/TPM ER treatment include, for example, polydipsia, polyphagia, polyuria, blurred vision, dizziness, extreme tiredness, genital itching, nausea and vomiting, frequent yeast infections, psoriasis, and slow healing of wounds.

Participants in the study included 475 high-risk overweight or obese patients with prediabetes and/or metabolic syndrome at baseline from the two-year SEQUEL study, for their progression to type 2 diabetes and their changes in cardiometabolic parameters. After 108 weeks, it was observed that patients receiving PHEN/TPM ER, in conjunction with lifestyle modifications, experienced significant weight loss along with markedly reduced progression to type 2 diabetes and improvements in multiple cardiometabolic disease risk factors.

Subjects in the PHEN/TPM ER Recommended dose (7.5 mg/46 mg) and Top dose (15 mg/92 mg) treatment groups experienced reductions of 70.5% and 78.7% in the annualized incidence rate of type 2 diabetes, respectively, versus placebo, which was related to degree of weight lost (10.9% and 12.1%, respectively, versus 2.5% with placebo; ITT-MI; $P<0.0001$). PHEN/TPM ER therapy was well tolerated by this subgroup over two years.

Subgroup analysis of patients participating in the CONQUER and SEQUEL studies was performed as described herein. (See also, Garvey et al., *Diabetes Care* 2014; 37(4): 912-21). The analysis allowed for assessment of the ability of PHEN/TPM ER to prevent progression to type 2 diabetes in at-risk patients during a 2-year period. In patients with prediabetes and/or MetS, PHEN/TPM ER was highly effective in inducing and sustaining weight loss and had a profound effect on prevention of type 2 diabetes, as measured by cumulative and annualized incidence rates. There was a 71% and 79% reduction in progression to type 2 diabetes among patients treated with 7.5/46 and 15/92 compared with placebo over 108 weeks. Weight loss associated with PHEN/TPM ER treatment may be maintained beyond 2 years and may lead to sustained lower rates of progression to type 2 diabetes as compared with patients treated with placebo. Most cases of type 2 diabetes in PHEN/TPM ER-treated patients occurred in the first year of the study, whereas cases continued to accumulate into the second year in the placebo group (FIG. 2A); thus, the difference in cumulative incidence between the PHEN/TPM ER and placebo groups, and the relative degree of type 2 diabetes prevention, may continue to increase over time.

The ability to prevent type 2 diabetes correlated with the magnitude of weight loss, independent of randomization group. The annualized incidence rate for type 2 diabetes was progressively reduced as weight loss increased, with the lowest value realized at ≥15% weight loss, suggesting that greater weight loss is associated with greater benefits. Previous studies of lifestyle intervention have also indicated that the degree of weight loss was an important determinant of type 2 diabetes prevention (Hamman R F, et al., *Diabetes Care* 2006; 29(9):2102-2107). The results discussed herein are in agreement with demonstrate that greater weight loss leads to greater reductions in the rate of type 2 diabetes. All categories with ≥5% weight loss experienced greater reductions in cumulative type 2 diabetes incidence when compared with the weight loss category of <5%. Thus, while modest weight loss of approximately 5%, as recommended by the ADA, is beneficial, greater degrees of weight loss appear to lead to greater prevention of type 2 diabetes.

Although the present study was limited to 2 years, the DPP, Finnish Diabetes, (Laaksonen D E, et al., *Diabetes* 2005; 54(1):158-165) and Da Qing studies all demonstrated that after changes in or discontinuation of active treatment, the incidence of new type 2 diabetes diagnoses remained reduced compared with placebo or usual care over longer periods of follow-up (Pan X R, et al., *Diabetes Care* 1997; 20(4):537-544, Lindstrom J, et al., *Lancet* 2006; 368(9548): 1673-1679, Christophi C A, et al., *Lancet* 2009; 374(9702): 1677-1686 and Li G, et al., *Lancet* 2008; 371(9626):1783-1789. Based on these data, reduced rates of type 2 diabetes should continue to be observed in the PHEN/TPM ER treatment arms compared with placebo, even after discontinuation of drug treatment.

Importantly, weight loss and prevention of type 2 diabetes as a consequence of PHEN/TPM ER therapy were accompanied by an increase in insulin sensitivity, as manifested by reduced glucose and insulin values, and improvements in cardiometabolic risk factors (blood pressure, waist circumference, triglycerides, and HDL-C). Furthermore, systemic inflammation, as measured by hs-CRP and fibrinogen at week 56, was reduced, and levels of the insulin-sensitizing adipocytokine, adiponectin, at week 56, were increased. Since insulin resistance, dyslipidemia, inflammation, and dysregulated secretion of adipocytokines are all hallmarks of cardiometabolic disease, these findings are indicative of the potential reversal of this pathophysiologic process.

It should be noted that in clinical trials assessing PHEN/TPM ER, all patients received advice on lifestyle modification, and the current benefits reflect the combination of PHEN/TPM ER and the lifestyle program (Gadde et al., Lancet 2011, Garvey et al., Am J Clin Nutr 2012; 95(2): 297-308). The LEARN program is similar to the DPP lifestyle intervention in that it strongly emphasizes behavior modification; however, the LEARN program has a less stringent calorie-reduction requirement (decrease of 500 kcal vs 750-1000 kcal in DPP) and encourages a progressive increase in exercise, rather than specifying a minimum amount of physical activity, as in DPP. Although the differences between lifestyle intervention alone (placebo group) and PHEN/TPM ER with lifestyle intervention to promote weight loss and prevent type 2 diabetes were relatively small in the SEQUEL trial, treatment with PHEN/TPM ER should nevertheless be combined with lifestyle modification to realize the full clinical benefits demonstrated in this study.

These findings have particular relevance to real world treatment decisions, since maintaining clinically meaningful weight loss through lifestyle changes alone is challenging (Norris S L, et al., *Cochrane Database Syst Rev* 2005; 18(2):CD005270). The robust clinical benefits observed with an effective pharmacologic agent combined with lifestyle modification thus may confer a significant advantage to improve outcomes in patients at high risk of developing type 2 diabetes.

In general, PHEN/TPM ER was well tolerated, with no meaningful differences in safety in the prediabetes and/or MetS cohort during 108 weeks when compared with the overall SEQUEL population, and no differences between years 1 and 2 (Garvey et al., *Am J Clin Nutr* 2012; 95(2): 297-308). Given the high risk of type 2 diabetes, which confers extensive patient suffering and high societal costs, the potential benefit:risk ratio of weight-loss treatment could be particularly favorable in patients with prediabetes and/or MetS.

The SEQUEL study was limited to high-enrolling centers with high patient retention from CONQUER, so not all patients were eligible for the extension (Garvey et al., *Am J Clin Nutr* 2012; 95(2):297-308). Patients enrolled at sites eligible to participate in SEQUEL had slightly greater weight loss (~1% across treatment arms) at CONQUER end point than patients at non-SEQUEL sites. In addition, a higher percentage of PHEN/TPM ER-treated patients elected to continue in the study, so the original 2:1:2 randomization ratio was not maintained in the SEQUEL trial. The overall enrolled population for the SEQUEL clinical trial was larger than the subset of patients evaluated in this subanalysis; even so, baseline demography, efficacy, and safety were similar to the overall population, suggesting continuity across populations (Gadde et al., *Lancet* 2011, Garvey et al., Am J Clin Nutr 2012; 95(2):297-308). Because patients with type 2 diabetes were excluded, there were some significant differences, mostly in glycemic parameters, between the cohort included in this analysis and those who were excluded (Table 4).

means that the study is largely representative of the type of care given in routine clinical practice, indicating that clinical benefits seen here may also be achieved in a real-world setting (3). In a separate analysis of the overall SEQUEL population, including those with type 2 diabetes, the weight loss associated with PHEN/TPM ER treatment induced improvement in cardiometabolic parameters even as use of medications to treat dysglycemia, hypertension, and dyslipidemia was reduced as compared with placebo (40). This suggests that weight loss associated with PHEN/TPM ER may lead to reduced medication burden for the treatment of weight related comorbidities. Lastly, while 2 years is longer than any registration studies, it would be beneficial to have longer term data to add to our understanding of the benefits and risks of prolonged PHEN/TPM ER use.

This study demonstrates that PHEN/TPM ER plus lifestyle modification was generally well tolerated and produced significant weight loss through 108 weeks in patients with prediabetes and/or MetS at baseline. The ability of PHEN/TPM ER to prevent progression to type 2 diabetes was profound, with both PHEN/TPM ER treatment groups exhibiting statistically significant reductions in incidence rate in these high-risk individuals with prediabetes and/or MetS, with greater weight loss leading to greater reductions in progression to type 2 diabetes. Concomitant improvements in glucose homeostasis, insulin sensitivity, and cardiometabolic-disease biomarkers were also seen. These data indicate that adding PHEN/TPM ER to lifestyle modification may constitute a new and effective therapeutic approach in patients with obesity and cardiometabolic disease, even as an alternative to bariatric surgery, by virtue of the ability of PHEN/TPM ER to produce substantial weight loss and to reduce risk of progression to type 2 diabetes in patients at high risk.

Of the 866 subjects who completed CONQUER at eligible SEQUEL sites, 675 (77.9%) elected to enroll in the SEQUEL extension study (Garvey et al., *Am J Clin Nutr* 2012; 95:297-308). The SEQUEL cohort included 145

TABLE 4

Baseline demographics of patients included vs. those excluded from the analysis

| Parameter | Prediabetes and/or Metabolic Syndrome Cohort (n = 475) Mean (SD) | Excluded Cohort (n = 1973) Mean (SD) | P Value |
| --- | --- | --- | --- |
| Age (years) | 52.0 (10.4) | 50.9 (10.4) | 0.0457 |
| Women, n (%) | 308 (64.8) | 1404 (71.2) | 0.0070 |
| HDL-C (mmol/mol) | 1.2 (0.3) | 1.2 (0.4) | 0.0100 |
| Fasting glucose, mmol/L | 5.7 (0.7) | 5.9 (1.3) | 0.0007 |
| $HbA_{1c}$ (%) [mmol/L (SD)] | 5.7 (0.5) [39 (4.0)] | 5.9 (0.8) [41 (8.7)] | <0.0001 |
| Subjects with antidiabetic medication use, n (%) | 4 (0.8) | 249 (12.6) | <0.0001 |
| Subjects with lipid-lowering medication use, n (%) | 194 (40.8) | 700 (35.5) | 0.0293 |

Also, because the study involved active management to standards of care, changes in concomitant medications for treatment of hypertension, dyslipidemia, and hyperglycemia are likely to have affected related study variables, often narrowing the gap between PHEN/TPM ER-treated patients and those taking placebo. However, active management was applied by treatment-blinded clinicians across placebo and PHEN/TPM ER treatment groups. Although these medication adjustments may affect some parameters, this also (21.5%) subjects with type 2 diabetes at baseline and 55 (8.1%) subjects who did not meet criteria for either prediabetes or MetS; these individuals were excluded from the current analysis, leaving 475 (70.4%) at-risk subjects as defined by either prediabetes or MetS criteria, including 316 with prediabetes, 451 with MetS, and 292 meeting criteria for both prediabetes and MetS. Baseline demographics and clinical characteristics for subjects with prediabetes and/or MetS were similar among the treatment arms (Table 1).

TABLE 1

Baseline demographics and clinical characteristics of the cohort with prediabetes and/or MetS at baseline (ITT).

| Demographic or clinical characteristics | Placebo (n = 159) | PHEN/TPM 7.5/46 (n = 115) | PHEN/TPM 15/92 (n = 201) |
|---|---|---|---|
| Mean age, years (SD) | 52.5 (9.7) | 52.4 (10.9) | 51.3 (10.5) |
| Women, n (%) | 101 (63.5) | 75 (65.2) | 132 (65.7) |
| Race, n (%) | | | |
| Caucasian | 139 (87.4) | 102 (88.7) | 169 (84.1) |
| Black | 19 (11.9) | 11 (9.6) | 27 (13.4) |
| Other | 2 (1.3) | 3 (2.6) | 7 (3.5) |
| Mean weight, kg (SD) | 102.9 (19.0) | 104.4 (18.3) | 103.4 (17.8) |
| Mean BMI, kg/m² (SD) | 36.1 (4.5) | 36.2 (4.5) | 36.3 (4.4) |
| Mean waist circumference, cm (SD) | 113.7 (12.9) | 113.4 (12.3) | 113.1 (11.9) |
| Mean blood pressure (mmHg) | | | |
| Systolic (SD) | 129.1 (14.4) | 127.8 (12.0) | 128.1 (13.0) |
| Diastolic (SD) | 80.9 (9.5) | 80.5 (9.2) | 80.5 (8.4) |
| Mean heart rate, bpm (SD) | 70.4 (10.9) | 72.8 (9.9) | 72.5 (10.3) |
| Mean total cholesterol, mg/dL (SD) | 205.7 (41.9) | 203.6 (35.6) | 204.0 (40.4) |
| Mean LDL-C, mmol/L (SD) | 3.3 (0.9) | 3.2 (0.8) | 3.2 (0.9) |
| Mean non-HDL-C, mmol/L (SD) | 4.1 (1.1) | 4.0 (0.9) | 4.1 (1.0) |
| Mean HDL-C, mmol/L (SD) | 1.2 (0.3) | 1.3 (0.3) | 1.2 (0.28) |
| Mean triglycerides, mmol/L (SD) | 1.8 (0.7) | 1.8 (0.8) | 1.8 (0.8) |
| Mean fasting glucose, mmol/L (SD) | 5.7 (0.7) | 5.8 (0.7) | 5.7 (0.8) |
| Mean glycated hemoglobin, % (SD) (mmol/mol (SD)) | 5.7 (0.5) (39 (5.5)) | 5.7 (0.4) (39 (4.4)) | 5.7 (0.5) (39 (5.5)) |
| Fasting insulin, pmol/L (SD) | 122.2 (80.6) | 122.2 (90.3) | 119.5 (67.4) |
| Mean hs-CRP, mg/L (SD) | 5.4 (6.7) | 6.6 (10.6) | 6.2 (7.8)† |
| Subjects with antidiabetes medication use, n (%) | 1 (0.6) | 1 (0.9) | 2 (1) |
| Subjects with antihypertensive medication use, n (%) | 106 (66.7) | 69 (60.0) | 124 (61.7) |
| Subjects with lipid-lowering medication use, n (%) | 64 (40.3) | 49 (42.6) | 81 (40.3) |

LDL-C, LDL cholesterol.
*Defined as subjects with prediabetes, MetS, or both at baseline.
†There were missing values for hs-CRP for one subject in the 15/92 group.

Treatment with PHEN/TPM ER induced significantly greater weight loss versus placebo in subjects in the prediabetes and/or MetS cohort. After 108 weeks of treatment, this cohort lost 10.9% and 12.1% of their body weight in the 7.5/46 and 15/92 treatment arms, respectively, versus 2.5% in those subjects receiving placebo (ITT-MI; P<0.0001), with similar results in the ITT-LOCF analysis (FIG. 1). The degree of weight loss in the placebo and PHEN/TPM ER treatment arms was similar in subjects with prediabetes or MetS at baseline and in the overall SEQUEL population at week 108 (26). No subjects experienced a BMI less than 18.5 kg/m2 at study end. For FIG. 1, P<0.0001 vs placebo for all time points assessed. LS, least-squares; LOCF, last observation carried forward; MI, multiple imputation; PHEN/TPM ER, phentermine and topiramate extended-release.

Figure 2C:
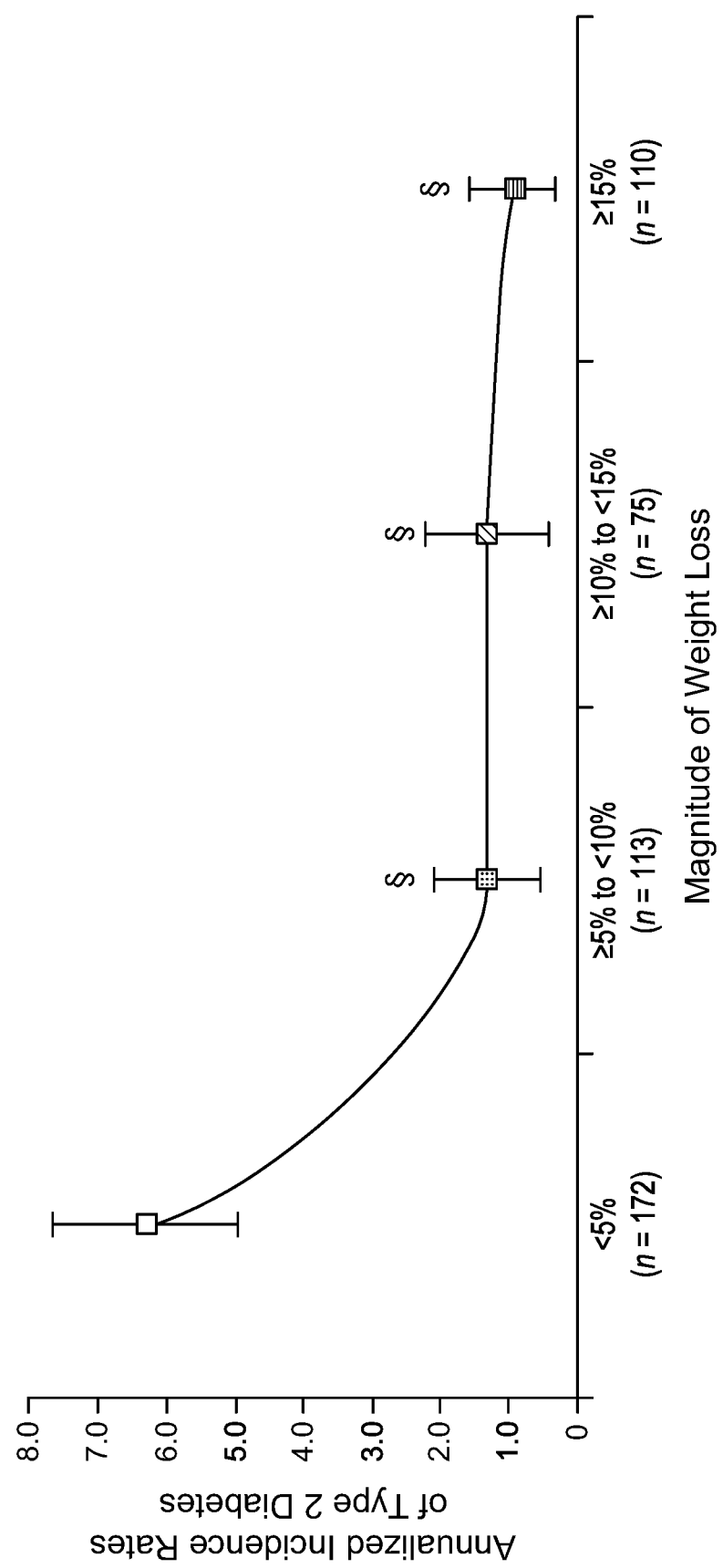
FIG. 2C shows the relationship between weight loss and type 2 diabetes incidence at study end in the prediabetes and/or Metabolic Syndrome cohort of the SEQUEL study (ITT-MI).

Although subjects in all treatment arms with prediabetes and/or MetS were administered a moderate lifestyle intervention program, the cumulative incidence rates of type 2 diabetes (FIG. 2A) was markedly reduced in subjects randomized to PHEN/TPM ER when compared with placebo over 108 weeks. The annualized incidence rate of type 2 diabetes in this population was 6.1, 1.8, and 1.3 for placebo, 7.5/46, and 15/92 (reductions of 70.5% with 7.5/46 and 78.7 with 15/92; P<0.05 vs placebo; ITT). The absolute risk reduction of progression to type 2 diabetes was 11.4%, 3.5%, and 2.5% for placebo, 7.5/46 (95% CI: 1.8%, 13.9% vs placebo), and 15/92 (95% CI: 3.5%, 14.3% vs placebo). In subjects meeting criteria for prediabetes, subjects receiving 7.5/46 had a 48.6% reduction in the annualized incidence rate of type 2 diabetes and those receiving 15/92 had an 88.6% reduction versus placebo (FIG. 2B). Furthermore, subjects with MetS receiving 7.5/46 had a 76.6% reduction and those receiving 15/92 had a 79.7% reduction (FIG. 2B). The magnitude of effect for type 2 diabetes prevention was related to the degree of weight loss achieved at 108 weeks in the ITT-MI population (FIG. 2C). Error bars represent 95% CI. Annualized incidence rate of type 2 diabetes was based on first occurrence of 2 consecutive FG≥7.0 mmol/L, 2 consecutive OGTT≥11.1 mmol/L, or taking antidiabetic medications at end point. Greater weight loss was associated with a greater reduction in incidence of type 2 diabetes regardless of randomization group. Subjects achieving <5% weight loss had the highest annualized type 2 diabetes incidence rate: 6.3. The lowest incidence rate, 0.9, was observed with weight loss of ≥15%; an intermediate type 2 diabetes incidence rate of 1.3 was seen among those with ≥5% to <10% or ≥10% to <15% weight loss (ITT-MI; P<0.05 vs <5% weight loss for all comparisons). In the ITT-LOCF analysis, annualized incidence rate of type 2 diabetes was 6.1 (SD: 1.3), 1.8 (SD: 0.9), 0.6 (SD: 0.6), and 1.3 (SD: 0.8) for the <5%, ≥5% to <10%, ≥10% to <15%, and ≥15% groups, respectively. For FIGS. 2A-2C *P=0.0125 vs placebo; †P=0.0093 vs placebo; ‡P=0.0007 vs placebo; §P<0.05 vs <5% weight loss for all comparisons. ITT is intent to treat; CI is confidence interval; FG is fasting glucose; OGTT is oral glucose tolerance test; and PHEN/TPM ER is phentermine and topiramate extended-release.

Figure 3A:
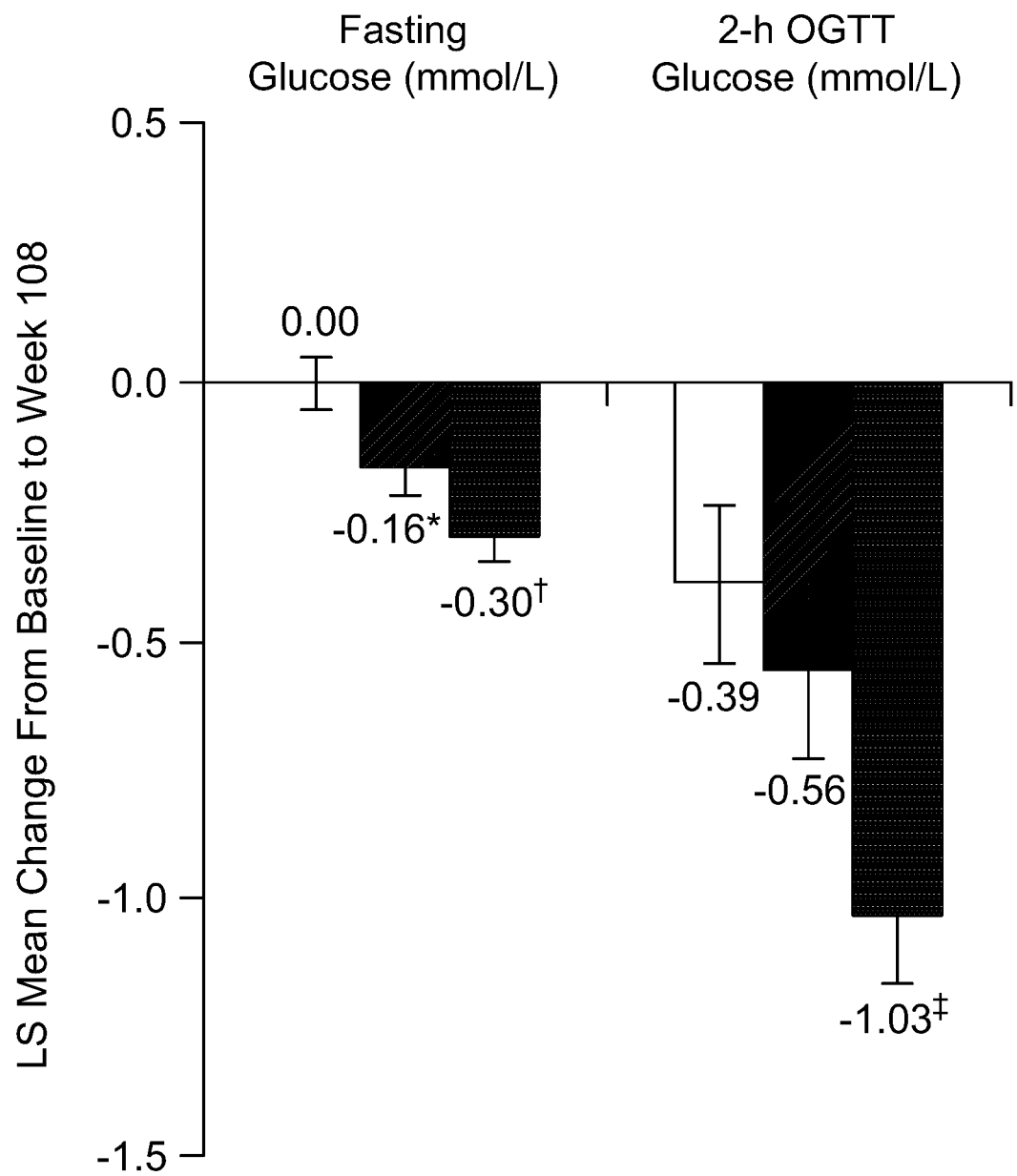
FIG. 3A shows least-squares mean percent change from baseline in glucose in subjects in the prediabetes and/or Metabolic Syndrome cohort.
Figure 3B:
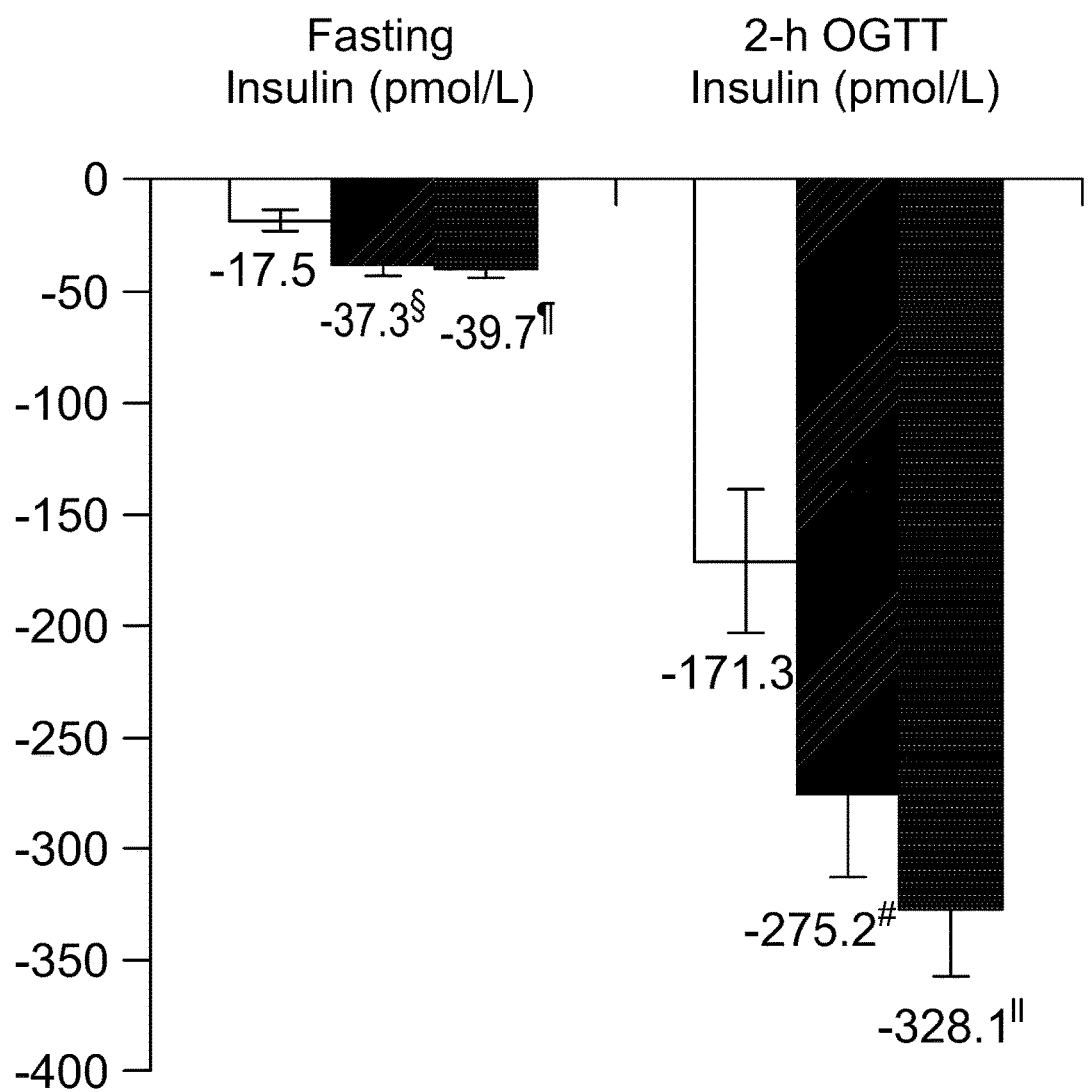
FIG. 3B shows least-squares mean percent change from baseline in insulin in the prediabetes and/or Metabolic Syndrome cohort.
Figure 4:
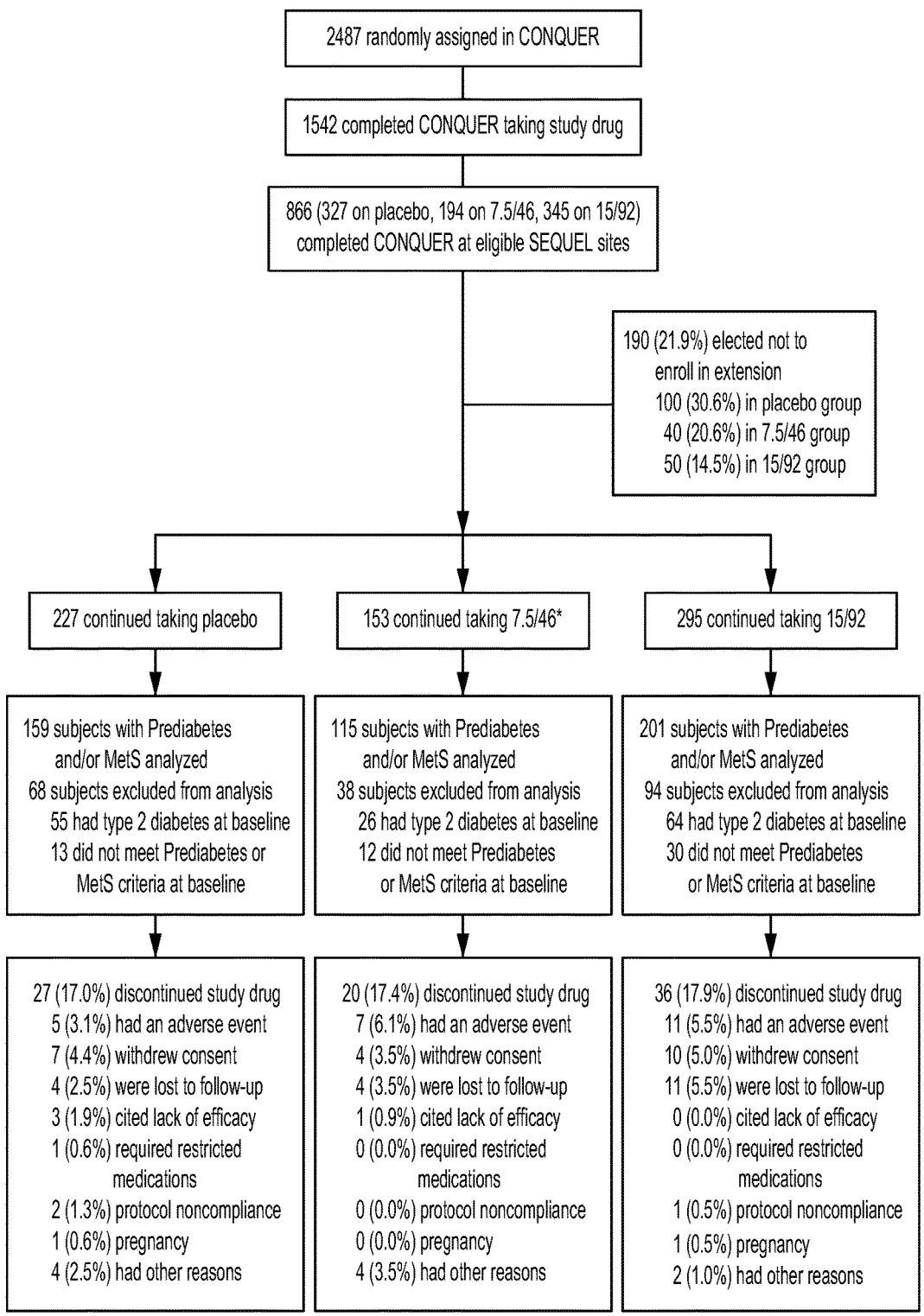
FIG. 4 shows a diagram of the trial profile.

PHEN/TPM ER also significantly improved cardiometabolic disease risk factors versus placebo in subjects with prediabetes and/or MetS. As shown in FIGS. 3A-C, which show glycemic and lipid parameters at week 108 in the cohort with prediabetes and/or Metabolic Syndrome at baseline, when compared with placebo, fasting glucose, fasting insulin, 2-hour post-OGTT glucose, fasting triglycerides, and HDL-C were all improved in the PHEN/TPM ER groups over 108 weeks (ITT-MI). Reductions in SBP (mm Hg) of −3.9 (SE: 0.98), −5.0 (SE: 1.14), −5.1 (SE: 0.91) and reductions in DBP of −3.7 (SE: 0.73), −3.6 (SE: 0.82), and −3.8 (SE: 0.61), were observed with placebo, 7.5/46, and 15/92, respectively (not significant vs placebo; ITTMI; Table 2). Subjects treated with PHEN/TPM ER also had reduced waist circumference, HbA1c, and Homeostasis Model of Assessment-Insulin Resistance and increased Whole Body Insulin Sensitivity Index versus placebo at week 108 (ITT-MI; Table 2). Data represent least-squares mean change in subjects with prediabetes or Metabolic Syndrome at baseline, intent-to-treat with multiple imputation. HOMA-IR is Homeostasis Model of Assessment-Insulin Resistance; WBISI is Whole Body Insulin Sensitivity Index.

significantly greater percentage of subjects treated with 7.5/46 (22.4%) and 15/92 (27.6%) achieved remission of MetS compared with placebo (9.2%; P=0.0001 vs placebo). Also, at week 56 in subjects with prediabetes and/or MetS, PHEN/TPM ER was associated with lower hs-CRP values (−1.7, −2.7, and −2.2 mg/dL in placebo, 7.5/46, and 15/92, respectively; P=not significant vs placebo; ITT-MI), lower fibrinogen levels (−10.1, −11.3, and −15.2 mg/dL in placebo, 7.5/46, and 15/92; P=not significant vs placebo; ITT-MI), and increased adiponectin concentrations (0.4, 2.2, and 2.9 Og/mL in placebo, 7.5/46, and 15/92; P<0.0001 vs placebo; ITT-MI). In FIGS. 3A-C error bars represent 95% CI. *P=0.0474; †P<0.0001; ‡P=0.0028; §P=0.0126; ¶P=0.0012, #P=0.0419; ||P=0.0004; **P=0.0262; ††P=0.0009 vs placebo for all comparisons. ITT, intent to treat; MI, multiple imputation; CI, confidence interval; OGTT, oral glucose tolerance test; LS, least-squares; PHEN/TPM ER, phentermine and topiramate extended-release; HDL, high-density lipoprotein.

TABLE 2

Changes from baseline to week 108 in secondary end points in the cohort with prediabetes and/or Metabolic Syndrome at baseline (ITT-MI).

|  | Placebo (n = 159) | PHEN/TPM ER 7.5/46 (n = 115) | PHEN/TPM ER 15/92 (n = 201) |
|---|---|---|---|
| Mean waist circumference, cm (SE) | −4.6 (0.65) | −11.3 (0.76)* | −12.8 (0.58)* |
| Mean HbA$_{1c}$, % (SE) [mmol/mol (SE)] | 0.07 (0.02) [0.8 (0.2)] | −0.03 (0.03) [−0.3 (0.3)]† | −0.09 (0.02) [−1.0 (0.2)]* |
| Mean systolic blood pressure, mm Hg (SE) | −3.9 (0.98) | −5.0 (1.14) | −5.1 (0.91) |
| Mean diastolic blood pressure, mm Hg (SE) | −3.7 (0.73) | −3.6 (0.82) | −3.8 (0.61) |
| Mean HOMA-IR (SE) | −0.8 (0.21) | −1.7 (0.25)‡ | −1.8 (0.21)§ |
| Mean WBISI (SE) | 1.6 (0.36) | 2.4 (0.47) | 3.4 (0.33)¶ |

*P < 0.0001,
†P = 0.0037,
‡P = 0.0047,
§P = 0.0006,
¶P = 0.0003 vs placebo for a comparisons.

Similar results were seen in the ITT-LOCF analysis (Table 3). Among those with MetS at baseline, by week 108, a

TABLE 3

Changes from baseline to week 108 in secondary end points in the cohort with prediabetes and/or Metabolic Syndrome at baseline (ITT-LOCF).

|  | Placebo (n = 159) | PHEN/TPM ER 7.5/46 (n = 115) | PHEN/TPM ER 15/92 (n = 201) |
|---|---|---|---|
| Mean waist circumference, cm (SE) | −4.4 (0.63) | −11.4 (0.74)* | −12.9 (0.56)* |
| Mean fasting glucose, mmol/L (SE) | 0.01 (0.05) | −0.18 (0.06)† | −0.32 (0.04)* |
| Mean 2-hour OGTT glucose, mmol/L (SE) | −0.37 (0.14) | −0.57 (0.16) | −1.01 (0.12)‡ |
| Mean HbA$_{1c}$, % (SE) [mmol/mol (SE)] | 0.08 (0.02) [0.9 (0.2)] | −0.03 (0.02) [−0.3 (0.2)]§ | −0.09 (0.02) [−1.0 (0.2)]* |
| Mean fasting insulin, pmol/L (SE) | −18.4 (5.0) | −39.2 (5.9)¶ | −37.3 (4.5)# |
| Mean 2-hour OGTT insulin, pmol/L (SE) | −157.2 (30.7) | −264.0 (36.1)|| | −3.270 (27.3)* |
| Mean systolic blood pressure, mm Hg (SE) | −4.1 (0.92) | −4.9 (1.08) | −5.2 (0.82) |
| Mean diastolic blood pressure, mm Hg (SE) | −3.7 (0.66) | −3.2 (0.77) | −3.8 (0.58) |
| Mean HOMA-IR (SE) | −0.8 (0.21) | −1.7 (0.25)** | −1.7 (0.19)†† |
| Mean WBISI (SE) | 1.5 (0.42) | 2.8 (0.49)‡‡ | 3.6 (0.37)§§ |
| Mean non-HDL-C, % (SE) | −9.1 (0.42) | −9.9 (1.67) | −10.0 (1.26) |

TABLE 3-continued

Changes from baseline to week 108 in secondary end points in the cohort with prediabetes and/or Metabolic Syndrome at baseline (ITT-LOCF).

|  | Placebo (n = 159) | PHEN/TPM ER 7.5/46 (n = 115) | PHEN/TPM ER 15/92 (n = 201) |
|---|---|---|---|
| Mean HDL-C, % (SE) | 6.6 (1.54) | 10.0 (1.81) | 14.2 (1.37)[§§] |
| Mean triglycerides, % (SE) | −1.1 (2.77) | −13.3 (3.26)[¶¶] | −17.7 (2.46)* |

*$P < 0.0001$,
[†]$P = 0.011$,
[‡]$P = 0.005$,
[§]$P = 0.0015$,
[¶]$P = 0.0075$,
[#]$P = 0.0052$,
[‖]$P = 0.025$,
**$P = 0.0087$,
[††]$P = 0.0033$,
[‡‡]$P = 0.04441$,
[§§]$P = 0.0002$,
[¶¶]$P = 0.0047$ vs placebo for all comparisons.

The daily dose of, phentermine, can be any appropriate daily dose. For example, the daily dose of the sympathomimetic agent, for example, phentermine, can be from about 2 mg to about 1,500 mg, for example, a daily dose of about 2 mg to about 20 mg. The daily dose of the sympathomimetic agent can be increased if and when the daily dose of topiramate is increased, although this is not required unless otherwise specified. The ratio of topiramate to phentermine in the different daily doses may be constant, for example, if the first daily dose is 23 mg of topiramate and 3.75 mg phentermine, for a weight of phentermine to topiramate ratio of about 16% (i.e. the weight of the phentermine is about 16% of the weight of the topiramate), then one or more of the second, third, and fourth daily doses can also have about a 16% weight ratio of phentermine to topiramate. Other ratios may also be used, for example, about 10-20%, about 13-17%. The ratio may be maintained for one or more of the second, third and fourth doses. For example, the second daily dose may be about 7.5 mg phentermine and 46 mg topiramate, the third may be about 11.25 mg phentermine and about 69 mg topiramate and the fourth about 15 mg phentermine and about 92 mg topiramate, each daily dose having a ratio of about 16% (the weight of phentermine being about 16% of the weight of phentermine).

Subjects who are candidates to maintain either the daily dose of 46 mg topiramate with 7.5 mg phentermine or the daily dose of 92 mg topiramate with 15 mg phentermine can maintain that regimen. Subjects who respond to the 7.5 mg phentermine/46 mg topiramate daily dose may continue taking that daily dose after the 3 month period for an additional period of time, for example, for 3, 6, 9, 12, 18, 24, or 36 additional months or more.

The phentermine and topiramate used in the dosing regimens and methods described herein can be administered in any suitable dosage form, depending on the desired route of administration. For example, tablets, capsules, caplets, elixirs, syrups, sachets, granules, powders, pellets, and beads are all suitable for oral administration. Dosage forms for these and other routes and modes of administration are discussed, for example, in *Remington: The Science and Practice of Pharmacy*, which is hereby incorporated by reference in its entirety.

Topiramate can be present in a controlled release dosage form, such as a sustained release form, a delayed release form, or a dosage form with both delayed and sustained release. Controlled release forms can be any controlled release form, and can be prepared by any preparation method known in the art. Some controlled release forms include topiramate dispersed within a matrix of one or more controlled release polymers, for example, one or more hydrolyzable or degradable polymers, such as one or more hydrophilic polymers. Other controlled release forms include a topiramate containing dosage form coated with one or more controlled release polymers. Exemplary hydrophilic polymers useful for this purpose include cellulose polymers, such as one or more of hydroxypropyl cellulose, hydroxyethyl cellulose, hydroxypropyl methyl cellulose, methyl cellulose (METHOCEL®), ethyl cellulose, cellulose acetate, cellulose acetate phthalate, and sodium carboxymethylcellulose, acrylic polymers and copolymers, such as polymers or copolymers of one or more of (meth)acrylic acid, methyl(meth) acrylate, and ethyl (meth)acrylate, vinyl polymers and copolymers, such polymers with one or more of polyvinyl pyrrolidone (POVIDONE® and POVIDONE® K30), polyvinyl acetate, and ethylene vinyl acetate.

Controlled release dosage forms, such as sustained release dosage forms, can also include additional excipients such one or more binders, diluents, bulking agents, glidents, lubricant, taste-modifying agents, flavorings, colorings, and the like. Such agents can be useful in the manufacturing process of the controlled release dosage form, commercially beneficial, for example, to provide a commercially desirable appearance, taste, or both. Many examples of such excipients are known in the art, and are discussed, for example, in *Remington: The Science and Practice of Pharmacy*, which is hereby incorporated by reference in its entirety.

Specific examples of controlled release dosage forms of topiramate include polymer matrices that contain the topiramate and a controlled release polymer, tablets coated with a controlled release polymer, osmotic tablets, and polymer coated beads. In one aspect controlled release topiramate beads are made using an extrusion spheronization process to produce a matrix core comprised of topiramate, 40.0% w/w; microcrystalline cellulose (AVICEL® PH102), 56.5% w/w; and METHOCEL™ A15 LV, 3.5% w/w. The topiramate cores are then coated with ethyl cellulose, 5.47% w/w, and Povidone K30, 2.39% w/w. Such dosage forms can be prepared by methods known in the art, for example, methods described in U.S. Pat. Pub. No. 2009/0304785, which is hereby incorporated by reference.

In one example the composition of the topiramate beads may be 36.85% w/w topiramate, 52.05% w/w microcrystalline cellulose, 3.22% w/w methylcellulose, 5.47% w/w ethyl cellulose, and 2.39% w/w polyvinylpyrrolidone (PVP).

The phentermine can be present in the same dosage form as the topiramate or in a different dosage form. When the phentermine is in a different dosage form from the topiramate, the type of dosage form used for the phentermine can be the same or different from the type of dosage form used for the topiramate. For example, topiramate can be present in a capsule and phentermine can be present in a solution. In that example, the topiramate can be administered orally and the phentermine can be administered intra-muscularly. As another example, the topiramate and phentermine can be present in the same dosage form, such as a powder, bead, or granule, or in the same unit dosage form, such as a capsule, or tablet. When present in a tablet form the tablet can be a multilayer table, for example, a bilayer tablet having an immediate release portion containing the phentermine and a sustained release portion containing the topiramate. A tablet-in-tablet formulation can also be used, where the core comprises a therapeutically effective amount of topiramate that is surrounded by a layer comprising a therapeutically effective amount of phentermine. The topiramate and phentermine can be in direct contact or may be separated by a barrier layer. The core can contain both topiramate and one or more pharmaceutically acceptable excipients. The tablet can be coated with a rapidly dissolving coating or film.

The phentermine can be administered in an immediate release form dosage form. An exemplary immediate release form is an inert bead, such as a non-pareil or sugar sphere, coated with the phentermine, to form one or more coated beads. Additional coating agents, such as film-formers, diluents, plasticizers, binders, coating aids, adhesion aids, and the like, can also be present in the coating of the phentermine coated beads. Further, additional coating layers, such as film-coats or topcoats, can be present either on top of the phentermine coating or between the inert bead and the phentermine coating. Phentermine coated beads can be, for example, mixed with one or more tableting excipients, such as one or more binders, lubricants, glidant, etc., and compressed into one or more tablets. Phentermine coated beads can also be prepared as one or more capsules, for example, by filling one or more capsule shells, such as gelatin capsule shells, with the phentermine coated beads. In one aspect, phentermine hydrochloride is coated onto sugar spheres to provide immediate release phentermine beads. These beads are combined with the topiramate beads described above and then encapsulated into each of a plurality of capsules, with each capsule containing 3.75 mg phentermine (as 4.92 mg phentermine HCl) and 23 mg topiramate or 7.5/46, 11.25/69 and 15/92.

When phentermine is in the same dosage form as the topiramate, such as a unit dosage form with topiramate and phentermine, the unit dosage form can contain a controlled release portion of topiramate and an immediate release portion of phentermine. For example, one or more polymer coated beads containing topiramate and one or more sympathomimetic agent coated beads can be present in the same dosage form. In active ingredients may include methylcellulose, sucrose, starch, microcrystalline cellulose, ethylcellulose, povidone, gelatin, talc, and titanium dioxide.

One or more dosage forms of topiramate and phentermine, for example, for use in one or more of the dosing regimens or methods described herein, such as the dosage forms described herein, can be packaged into a convenient packaging for delivery to or use by one or more physicians, subjects, nurses, health-care professionals, etc. Such packaging can include one or more sealed containers, each containing one or more dosage forms of topiramate, such as the dosage forms described herein.

Upon oral administration of a dose of PHEN-TPM-ER 15 mg/92 mg, the resulting mean plasma phentermine maximum concentration ($C_{max}$), time to $C_{max}$ ($T_{max}$), area under the concentration curve from time zero to the last time with measureable concentration ($AUC_{0-t}$), and area under the concentration curve from time zero to infinity ($AUC_{0-\infty}$) are 49.1 ng/mL, 6 hr, 1990 ng·hr/mL, and 2000 ng·hr/mL, respectively. A high fat meal does not affect phentermine pharmacokinetics for PHEN/TPM ER 15 mg/92 mg. Phentermine pharmacokinetics is approximately dose-proportional from PHEN/TPM ER 3.75 mg/23 mg to phentermine 15 mg/topiramate 100 mg. Upon dosing phentermine/topiramate 15/100 mg fixed dose combination capsule to steady state, the mean phentermine accumulation ratios for AUC and $C_{max}$ are both approximately 2.5.

Upon oral administration of a single Qsymia 15 mg/92 mg, the resulting mean plasma topiramate $C_{max}$, $T_{max}$, $AUC_{0-t}$, and $AUC_{0-\infty}$, are 1020 ng/mL, 9 hr, 61600 ng·hr/mL, and 68000 ng·hr/mL, respectively. A high fat meal does not affect topiramate pharmacokinetics for PHEN/TPM ER 15 mg/92 mg. Topiramate pharmacokinetics is approximately dose-proportional from PHEN/TPM ER 3.75 mg/23 mg to phentermine 15 mg/topiramate 100 mg. Upon dosing phentermine 15 mg/topiramate 100 mg fixed dose combination capsule to steady state, the mean topiramate accumulation ratios for AUC and $C_{max}$ are both approximately 4.0.

SEQUEL was a 52-week extension of the 56-week, phase 3, randomized, double-blind, parallel-group, placebo-controlled CONQUER trial (Gadde K M, et al., *Lancet* 2011; 377(9774):1341-1352 and Garvey W T, et al. *Am J Clin Nutr* 2012; 95(2):297-308.). The selection process for the 36 SEQUEL sites was based on high initial CONQUER enrollment and subject retention. Subject outcomes and randomization remained blinded during this process. All subjects who completed CONQUER on treatment at this subset of 36 sites were eligible to enroll in the SEQUEL extension study (Garvey et al. 2012). All subjects entering SEQUEL maintained their original randomized treatment assignment from CONQUER (in a 2:1:2 ratio, stratified by gender and diabetic status) of once-daily oral placebo, PHEN 7.5 mg/TPM ER 46 mg, or PHEN 15 mg/TPM ER 92 mg (placebo, 7.5/46, and 15/92, respectively), plus lifestyle-modification counseling based on the LEARN (lifestyle, exercise, attitudes, relationships, and nutrition) program (Brownell K. *The LEARN Program for Weight Management*. Dallas, Tex., The Life Style Company 2000), for an additional 52 weeks, resulting in 108 weeks of treatment. A computer-generated algorithm had been used to randomize subjects to study treatment at the beginning of the CONQUER study.

Investigators and subjects remained blinded to treatment assignment. Study drug compliance (assessed by count of capsules returned by subject) and lifestyle counseling were addressed at each study visit, conducted every 4 weeks. At baseline (CONQUER week 0), subjects were overweight or obese adults (aged 18-70 years), with body mass indices of 27-45 kg/m$_2$, and ≥2 of the following weight-related comorbidities: central adiposity, dyslipidemia, hypertension, or type 2 diabetes. Subjects were actively managed to standard of care for their comorbidities, including the option to add, discontinue, or dose-adjust medications. The trials were approved by each center's institutional review board and overseen by an independent data safety review board. All subjects provided written informed consent. The first subject was enrolled into this study on Dec. 6, 2008, and the last subject completed the study on Jun. 8, 2010.

The subgroup analyses presented in this article were performed on the subset of subjects with prediabetes and/or MetS at baseline who elected to enroll in the SEQUEL study. Subjects with a medical history of type 2 diabetes at baseline were excluded from this analysis. The criteria for prediabetes for the study were as defined by the American Diabetes Association: IFG (fasting glucose levels 100-125 mg/dL [5.6-6.9 mmol/L]) or IGT (blood glucose 140-199 mg/dL [7.8-11.0 mmol/L] 2 hours following 75-g glucose load during an oral glucose tolerance test [OGTT]). The diagnosis of MetS was made when ≥3 of the following 5 criteria were met: waist circumference ≥102 cm in men or ≥88 cm in women; triglycerides ≥150 mg/dL (1.7 mmol/L) or taking ≥1 lipid-lowering medication; high-density lipoprotein cholesterol (HDL-C) <40 mg/dL (1.0 mmol/L) in men or <50 mg/dL (1.3 mmol/L) in women or taking ≥1 lipid-lowering medication; systolic blood pressure (SBP) ≥130 mm Hg or diastolic blood pressure (DBP) ≥85 mm Hg or taking ≥1 antihypertensive medication; fasting glucose ≥100 mg/dL (5.6 mmol/L) or taking drug treatment for elevated glucose (Alberti et al., Circulation 2009; 120:1640-1645). The primary end point was percent weight loss from baseline, which was assessed after 108 weeks (or early termination) in the SEQUEL study. Prespecified secondary end points were assessed at baseline, week 56, and week 108 (or early termination) and included annualized incidence rate of progression to type 2 diabetes and changes in glycemia, lipid parameters, blood pressure, and waist circumference (25, 26). Remission of MetS, i.e., no longer meeting the diagnostic criteria as evidenced by satisfying only ≤2 of these criteria, at week 108 was also assessed. Finally, at week 56, high-sensitivity C-reactive protein (hs-CRP) and fibrinogen, both of which are inflammatory markers associated with MetS, were measured, as was adiponectin, which is decreased in subjects with obesity and cardiometabolic disease (Sutherland J P, et al. *Metab Syndr Relat Disord* 2004; 2(2):82-104).

For analyses of glucose and insulin as measured by OGTT (75-g loading dose), the change in each parameter from the pre-glucose loading dose sample to the sample obtained 2 hours after the glucose loading dose at each applicable visit was calculated. OGTT was measured at baseline, week 4, week 56, and week 108. Fasting blood glucose was measured at baseline and weeks 4, 16, 28, 40, 56, 48, 96, and 108. Subjects were considered to have progressed to type 2 diabetes if their blood glucose was ≥126 mg/dL under fasting conditions during ≥2 consecutive measurements and/or ≥200 mg/dL at 2 hours after an OGTT.

Statistical analysis. Primary and secondary end points were assessed in the intent-to-treat (ITT) population using analysis of covariance (ANCOVA) with terms for treatment group and baseline value. To accommodate missing data, multiple imputation (MI) was applied to all end points where missing data were apparent using, specifically, a 2-step imputation process with m=5 imputations per step (Elobeid M A, et al. *PLoS ONE* 2009; 4(8):e6624.). In the first step, data were imputed to create a monotone missing data pattern by using a Markov chain Monte Carlo algorithm. In the second step, remaining missing data were imputed using Rubin's regression method (Rubin D B. *Multiple Imputation for Nonresponse in Surveys*. Wiley Series in Probability and Mathematical Statistics. New York, John Wiley & Sons, 1987). The complete imputed datasets were then analyzed by ANCOVA as described above, and the results from analysis of the separate imputed datasets were pooled into single estimates and tested as described by Schafer (Schafer J L. *Analysis of Incomplete Multivariate Data*. (*Monographs on Statistics and Applied Probability* 72) London, Chapman & Hall/CRC, 1997).

While various embodiments have been described in detail in order to explain the invention, such embodiments are not intended to be limiting unless otherwise specified. Indeed, a person of skill in the art will recognize that modifications, additions, and substitutions can be implemented without altering the scope or spirit of the invention. For example, while embodiments featuring one or more sympathomimetic agents have been described with reference to phentermine and particular dosages thereof, other sympathomimetic agents can be used in appropriate dosages to achieve similar results.

The invention claimed is:

1. A method of delaying the progression from prediabetes to diabetes in a patient, comprising:
   (a) identifying a patient at risk for developing type 2 comprising determining that the patient has at least one of the following:
      (i) HbA1c levels that are between 5.7% and 6.4%;
      (ii) plasma glucose levels between 7.8 mmol/L and 11 mmol/L; and
      (iii) blood glucose levels less between 6.1 mmol/L and 7.0 mmol/L; and
   (b) administering to the patient an oral dosage form comprising immediate release phentermine and controlled release topiramate.

2. The method of claim 1 wherein the oral dosage form comprises:
   a) 3.75 mg immediate release phentermine in combination with 23 mg controlled release topiramate, or
   b) 7.5 mg immediate release phentermine in combination with 46 mg controlled release topiramate, or
   c) 11.25 mg immediate release phentermine in combination with 69 mg controlled release topiramate, or
   d) 15 mg immediate release phentermine in combination with 92 mg controlled release topiramate.

3. The method of claim 2 wherein the oral dosage form is administered to the patient for at least 3 months.

4. The method of claim 1 wherein a first oral dosage form is administered to the patient for 1 to 2 weeks and a second oral dosage form is administered to the patient for 3 months and wherein the first oral dosage form comprises 3.75 mg immediate release phentermine in combination with 23 mg controlled release topiramate and the second oral dosage form comprises 7.5 mg immediate release phentermine in combination with 46 mg controlled release topiramate.

5. The method of claim 1 further comprising continuing to administer the oral dosage form to the patient following the onset of type 2 diabetes and thereby reducing the severity of type 2 diabetes symptoms in the patient.

6. The method of claim 3 wherein the administering prevents the onset of type 2 diabetes in the patient for the at least 3 months.

7. The method of claim 6 wherein the onset of type 2 diabetes is prevented if the patient has at least one of the following after the at least 3 months:
   (i) HbA1c levels that are 6.4% or less;
   (ii) plasma glucose levels that are 11 mmol/L or less; and
   (iii) blood glucose levels that are 7.0 mmol/L or less.

8. The method of claim 1 further comprising achieving in the patient at least one of the following: lowering of hs-CRP values to less than 3.0 mg/L, lowering fibrinogen levels to at least 400 mg/dL and increasing adiponectin concentrations to a level that is higher than the level measured in the patient prior to administering the oral dosage form to the patient.

9. The method of claim 1 further comprising achieving in the patient an improvement in at least one of the following: fasting glucose levels, fasting insulin levels, 2-hour post-OGTT glucose levels, fasting triglycerides levels or HDL-C levels.

10. The method of any one of the preceding claims, wherein the patient has MetS.

11. The method of claim 10 wherein the step of identifying a patient having MetS comprises determining that the patient has at least three of the following:
   (i) waist circumference of at least 102 cm if the patient is male or at least 88 cm if the patient is female;
   (ii) triglyceride level of 150 mg/dL or higher;
   (iii) HDL cholesterol levels below 40 mg/dL if the patient is a male or below 50 mg/dL if the patient is a female or taking lipid lowering medication;
   (iv) systolic blood pressure of 130 mm Hg or greater, or diastolic blood pressure of 85 mm Hg or greater or taking antihypertensive medication; and
   (v) fasting blood glucose levels of 100 mg/dL or greater or taking medication for elevated glucose.

12. The method of claim 10 further comprising achieving in the patient at least one of the following: lowering of hs-CRP values to less than 3.0 mg/L, lowering fibrinogen levels to at least 400 mg/dL and increasing adiponectin concentrations to a level that is higher than the level measured in the patient prior to administering the oral dosage form to the patient.

13. The method of claim 10 further comprising continuing to administer the oral dosage form to the patient following the onset of type 2 diabetes and thereby reducing the severity of type 2 diabetes symptoms following onset of diabetes in the patient.

14. The method of claim 10 wherein the administering prevents the onset of type 2 diabetes in the patient the at least 3 months.

15. The method of claim 10 wherein the patient achieves remission of MetS.

16. The method of claim 10 further comprising achieving in the patient an improvement in at least one of the following over the measurements for the patient prior to administering the oral dosage form to the patient: fasting glucose levels, fasting insulin levels, 2-hour post-OGTT glucose levels, fasting triglycerides levels or HDL-C levels.

* * * * *